(12) United States Patent
Kilambi et al.

(10) Patent No.: US 9,359,651 B2
(45) Date of Patent: *Jun. 7, 2016

(54) PRODUCTION OF FERMENTABLE SUGARS AND LIGNIN FROM BIOMASS USING SUPERCRITICAL FLUIDS

(75) Inventors: Srinivas Kilambi, Duluth, GA (US); Kiran L. Kadam, Golden, CO (US)

(73) Assignee: Renmatix, Inc., King of Prussia, PA (US)

( * ) Notice: Subject to any disclaimer, the term of this patent is extended or adjusted under 35 U.S.C. 154(b) by 943 days.

This patent is subject to a terminal disclaimer.

(21) Appl. No.: 13/522,918

(22) PCT Filed: Jan. 19, 2011

(86) PCT No.: PCT/US2011/021726
§ 371 (c)(1),
(2), (4) Date: Jul. 18, 2012

(87) PCT Pub. No.: WO2011/091044
PCT Pub. Date: Jul. 28, 2011

(65) Prior Publication Data
US 2012/0291774 A1 Nov. 22, 2012

Related U.S. Application Data

(60) Provisional application No. 61/296,101, filed on Jan. 19, 2010.

(51) Int. Cl.
*C13K 13/00* (2006.01)
*C12P 7/10* (2006.01)
(Continued)

(52) U.S. Cl.
CPC . *C13K 13/00* (2013.01); *C12P 7/10* (2013.01); *C13K 1/02* (2013.01); *C13K 13/002* (2013.01);

(58) Field of Classification Search
None
See application file for complete search history.

(56) References Cited

U.S. PATENT DOCUMENTS 2,198,785 A 4/1940 Mohr et al.
2,356,500 A 9/1944 Boinot
(Continued)

FOREIGN PATENT DOCUMENTS

CN 101586136 A 11/2009
CN 101613377 A 12/2009
(Continued)

OTHER PUBLICATIONS

Kassnar, novel sustainable solvents for bioprocessing applications, 2008.*
(Continued)

*Primary Examiner* — Melvin C Mayes
*Assistant Examiner* — Stefanie Cohen
(74) *Attorney, Agent, or Firm* — Travis B. Gasa; Andrew G. Bunn; Ballard Spahr LLP

(57) ABSTRACT

Methods are disclosed for the continuous treatment of biomass comprising a pretreatment step, wherein said biomass is contacted with a first supercritical, near-critical, or sub-critical fluid to form a solid matrix and a first liquid fraction; and a hydrolysis step, wherein said solid matrix formed in said pretreatment step is contacted with a second supercritical or near-supercritical fluid to produce a second liquid fraction and a insoluble lignin-containing fraction. Also disclosed are apparatuses for the continuous conversion of biomass comprising a pretreatment reactor and a hydrolysis reactor associated with said pretreatment reactor.

30 Claims, 7 Drawing Sheets

(51) Int. Cl.
*C13K 1/02* (2006.01)
*D21C 3/22* (2006.01)
*D21C 1/00* (2006.01)
*D21C 11/00* (2006.01)

(52) U.S. Cl.
CPC .. *D21C 3/22* (2013.01); *D21C 1/00* (2013.01); *D21C 11/0007* (2013.01); *Y02E 50/16* (2013.01); *Y02P 20/544* (2015.11)

(56) References Cited

U.S. PATENT DOCUMENTS

| | | | |
|---|---|---|---|
| 2,516,833 | A | 8/1950 | Ant-Wuorinen |
| 2,681,871 | A | 6/1954 | Wallace |
| 2,759,856 | A | 8/1956 | Saums et al. |
| 2,801,939 | A | 8/1957 | Hignett et al. |
| 3,212,932 | A | 10/1965 | Hess et al. |
| 3,314,797 | A | 4/1967 | Hess et al. |
| 4,165,240 | A | 8/1979 | Enokizono et al. |
| 4,201,596 | A | 5/1980 | Church et al. |
| 4,427,453 | A | 1/1984 | Reitter |
| 4,468,256 | A | 8/1984 | Hinger |
| 4,556,430 | A | 12/1985 | Converse et al. |
| 4,612,286 | A | 9/1986 | Sherman et al. |
| 4,637,835 | A | 1/1987 | Nagle |
| 4,644,060 | A | 2/1987 | Chou |
| 4,699,124 | A | 10/1987 | Nagle |
| 5,125,977 | A | 6/1992 | Grohmann et al. |
| 5,705,369 | A | 1/1998 | Torget et al. |
| 6,211,422 | B1 | 4/2001 | DeSimone et al. |
| 6,569,640 | B1 | 5/2003 | Castor et al. |
| 6,921,820 | B2 | 7/2005 | Arai et al. |
| 7,262,331 | B2 | 8/2007 | van de Beld et al. |
| 7,955,508 | B2 * | 6/2011 | Allan et al. ............ 210/749 |
| 2007/0161095 | A1 | 7/2007 | Gurin |
| 2007/0267008 | A1 | 11/2007 | Funazukuri et al. |
| 2008/0015336 | A1 | 1/2008 | Cornish et al. |
| 2009/0056201 | A1 | 3/2009 | Morgan |
| 2009/0176979 | A1 | 7/2009 | Hara et al. |
| 2009/0288788 | A1 | 11/2009 | Castor |
| 2010/0069626 | A1 | 3/2010 | Kilambi |
| 2010/0175690 | A1 | 7/2010 | Nagahama et al. |
| 2011/0183394 | A1 | 7/2011 | Bell et al. |

FOREIGN PATENT DOCUMENTS

| | | |
|---|---|---|
| DE | 3225074 | 1/1984 |
| EP | 98490 | 1/1984 |
| EP | 1304412 | 4/2003 |
| EP | 1686192 | 8/2006 |
| GB | 2145090 | 3/1985 |
| JP | 2001095594 | 4/2001 |
| JP | 2003212888 | 7/2003 |
| JP | 2006255676 | 9/2006 |
| JP | 2006263527 | 10/2006 |
| JP | 2008011753 | 1/2008 |
| JP | 2008248202 | 10/2008 |
| JP | 2010042604 | 2/2010 |
| KR | 2009030967 | 3/2009 |
| WO | 8301958 | 6/1983 |
| WO | 9967409 | 12/1999 |
| WO | 2007120210 | 10/2007 |
| WO | 2008/050740 | 5/2008 |
| WO | 2010034055 | 4/2010 |
| WO | 2011091044 | 7/2011 |

OTHER PUBLICATIONS

Adschiri et al., "Noncatalytic Conversion of Cellulose in Supercritical and Sub-Critical Water", Journal of Chemical Engineering of Japan, 1993, 26(6): 676-680.

Adschiri et al., "Cellulose hydrolysis in supercritical water to recover chemicals", Reaction Engineering for Pollution Prevention, 2000, 205-220.

Arai et al., "(Abstract) Biomass conversion in supercritical water for chemical recycle", Enerugi, Shigen, 16(2), 1995, 175-180.

Ehara et al., "A comparative study on chemical conversion of cellulose between the batch-type and flow-type in supercritical water", Cellulose, 2002, vol. 9, 301-311.

Gong et al., "(Abstract) Study on hydrolysis and saccharification of microcrystalline cellulose in supercritical water", Xiandai Huagong, 30(2), 2010, 44-47.

Lee et al., "(Abstract) Hydrolysis of cellulose under subcritical and supercritical water using continuous flow system", Hwahak Konghak, 39(2), 2001, 257-263.

Luterbacher et al., "(Abstract) High-Solids Biphasic CO2-H2O Pretreatment of Lignocellulosic Biomass", Biotechnology and Bioengineering, 107(3), 2010, 451-460.

Malaluan et al., "Biomass conversion in supercritical water", Off. Proc. Comb. Conf., 6th Conf. Asia Pac. Confed. Chem. Eng., 21st Australas. Chem. Eng. Conf., vol. 1, 1993, 2091/1-214/1.

Matsunaga et al., "Super-rapid chemical conversion of sugi wood by supercritical and subcritical water treatment", Mokuzai Gakkaishi, 50(5), 2004, 325-32.

Mok et al., "(Abstract) Dilute acid hydrolysis of biopolymers in a semi-batch flow reactor at supercritical pressure", Energy from Biomass and Wastes, 13, 1990, 1329-1347.

Mosier et al., "(Abstract) Optimization of pH controlled liquid hot water pretreatment of corn stover", Bioresource Technology, 96(18), 2005, 1986-1992.

Nakata et al., "(Abstract) Bioethanol from cellulose with supercritical water treatment followed by enzymatic hydrolysis", Applied Biochemistry and Biotechnology, 129-132, 2006, 476-485.

Park et al., "(Abstract) Kinetics of cellulose decomposition under subcritical and supercritical water in continuous flow system", Korean Journal of Chemical Engineering, 19(6), 2002, 960-966.

Saka, "Supercritical fluids to biomass research", Cellulose Communications, 5(3), 1998, 129-35.

Saka et al., "Supercritical fluids to biomass research (II)", Cellulose Communications, 9(3), 2002, 137-43.

Saka et al., "Chemical conversion of various celluloses to glucose and its derivatives in supercritical water", Cellulose Communications, 6(3), 1999, 177-191.

Sasaki et al., "Cellulose Hydrolysis in Sub-Critical and Supercritical Water", Journal of Supercritical Fluids, 1998, 13:261-268.

Sasaki et al., "Super-rapid enzymatic hydrolysis of cellulose with supercritical water solubilization pretreatment", Kobunshi Ronbunshu, 58(10), 2001, 527-32.

Sasaki et al., "Dissolution and Hydrolysis of Cellulose in Subcritical and Supercritical Water", Industrial & Engineering Chemistry Research, 39(8), 2000, 2883-2890.

Sasaki et al., "Kinetics of cellulose conversion at 25 MPa in sub-and supercritical water", AIChE Journal, 50(1), 2004, 192-202.

Sera et al., "Development of saccharification techniques for cellulosic biomass", Hitz Giho, 68(2), 2008, 40-5.

Soederstroem et al., "(Abstract) Effect of Washing on Yield in One- and Two-Step Steam Pretreatment of Softwood for Production of Ethanol", Biotechnology Progress, 20(3), 2004, 744-749.

Srinivasan et al., "Pretreatment of Guayule Biomass Using Supercritical Carbon Dioxide-Based Method", Bioresource Technology, 101(24), 2010, 9785-9791.

Vick Roy et al., "Biomass hydrolysis with sulfur dioxide and water in the region of the critical point", Process Technology Proceedings, 3 Supercrit. Flud Technol., 1985, 397-444.

Zhao et al., "Fermentable hexose production from corn stalks and wheat straw with combined supercritical and subcritical hydrothermal technology", Bioresource Technology, 100(23), 2009, 5884-5889.

Zhao et al., "Combined supercritical and subcritical process for cellulose hydrolysis to fermentable hexoses", Environmental Science & Technology, 43(5), 2009, 1565-1570.

Zhao et al., "Supercritical pretreatment and hydrolysis of cellulose", Huaxue Xuebao, 66(20), 2008, 2295-2301.

Ehara, K., et al. "Decomposition behavior of cellulose in supercritical water, subcritical water, and their combined treatments," The Japan Wood Research Society. vol. 51, pp. 148-153 (2005).

(56) References Cited

OTHER PUBLICATIONS

Schacht, C., et al. "From plant materials to ethanol by means of supercritical fluid technology," The Journal of Supercritical Fluids, vol. 46 pp. 299-321 (2008).

Zhao, Y., et al. "Supercritical/subcritical technology for pretreatment and hydrolysis of stalks," Progress in Chemistry, vol. 19(11) (2007).

Second Office Action issued Nov. 14, 2014 for Chinese Patent Application No. 201180011545.7, which was filed on Jan. 19, 2011 and published as CN102859066 on Jan. 2, 2013 (Inventor—Kilambi; Application—Renmatix, Inc.) (pp. 1-12).

Li et al., "Interaction of Supercritical Fluids with Lignocellulosic Materials", Industrial Engineering Chemistry Research, American Chemical Society Res., Jul. 1988, 27(7):1301-1312.

International Patent Application No. PCT/US2011/021726, "International Preliminary Report on Patentability", Aug. 2, 2012 (12 pages).

International Patent Application No. PCT/US2011/021726, "International Search Report and Written Opinion", Jul. 5, 2011 (16 pages).

Zhao et al., "Supercritical hydrolysis of cellulose for oligosaccharide production in combined technology", Chemical Engineering Journal, Aug. 1, 2009, 150(2):411-417.

Perez JA, et al., "Optimizing Liquid Hot Water Pretreatment Conditions to Enhance Sugar Recovery from Wheat Straw for Fuel-Ethanol Production," *Fuel*, 87(17-18): 3640-3647 (2008).

U.S. Appl. No. 13/864,744, "Non-Final Office Action", mailed Sep. 20, 2013 (13 Pages).

Kassnar, "Novel Sustainable Solvents for Bioprocessing Applications", 2008 (307 pages).

Lu et al., "Two-step hydrolysis of Japanese beech as treated by semi-flow hot-compressed water", J. Wood Sci., 2009, vol. 55, 367-375.

Canadian Patent Application No. 2,769,746, Office Action, mailed Nov. 21, 2012 (2 pages).

* cited by examiner

Products yield @ different residence time (T= 377 °C)

PRODUCTION OF FERMENTABLE SUGARS AND LIGNIN FROM BIOMASS USING SUPERCRITICAL FLUIDS

CROSS REFERENCE TO RELATED APPLICATIONS

This is a U.S. national phase patent application under 35 U.S.C. 371 of International Patent Application No. PCT/US2011/021726 entitled "Production of Fermentable Sugars and Lignin from Biomass Using Supercritical Fluids" filed Jan. 19, 2011, which claims benefit of priority under PCT Article 8 of U.S. Provisional Application No. 61/296,101, titled "Production of Fermented Sugars and Lignin from Biomass Using Supercritical Fluids" filed on Jan. 19, 2010. Both applications are incorporated herein by reference in their entireties.

FIELD OF THE INVENTION

The present invention generally relates to supercritical or near-supercritical treatment of biomass. More particularly, it relates to processes for treating biomass to produce fermentable sugars and lignin using supercritical, near-supercritical, and/or subcritical fluids.

BACKGROUND OF THE INVENTION

Biomass, especially lignocellulosic biomass, is an important raw material and can be processed into fuels or industrial chemicals. Current art technologies are very time consuming and hence, capital intensive. Supercritical solvents, such as supercritical water and supercritical carbon dioxide, have been used in extracting various substances and facilitating chemical reactions. The useful applications of these value-added products increase the importance of supercritical fluid technology. Modifications to prior art techniques are needed to improve the efficiency of converting of biomass from renewable resources and/or waste materials to more valuable products. The methods and apparatus of the present invention are directed toward these, as well as other, important ends.

SUMMARY OF THE INVENTION

In one embodiment, the invention is directed to methods for the continuous treatment of biomass, comprising:
a pretreatment step, wherein said biomass is contacted with a first supercritical, near-critical, or sub-critical fluid to form a solid matrix and a first liquid fraction;
wherein said first supercritical, near-critical, or sub-critical fluid comprises water and, optionally, $CO_2$; and
wherein said first supercritical, near-critical, or sub-critical fluid is substantially free of $C_1$-$C_5$ alcohol; and
a hydrolysis step, wherein said solid matrix is contacted with a second supercritical or near-supercritical fluid to produce a second liquid fraction (including soluble sugars and soluble lignin) and a insoluble lignin-containing fraction;
wherein said second supercritical or near-critical fluid comprises water and, optionally, $CO_2$; and
wherein said second supercritical or near-critical fluid is substantially free of $C_1$-$C_5$ alcohols.

In another embodiment, the invention is directed to methods for the continuous treatment of biomass, comprising:
a pretreatment step, wherein said biomass is contacted with a first supercritical, near-critical, or sub-critical fluid to form a solid matrix and a first liquid fraction;
wherein said first supercritical, near-critical, or sub-critical fluid comprises water and, optionally, $CO_2$; and
wherein said first supercritical, near-critical, or sub-critical fluid is substantially free of $C_1$-$C_5$ alcohol; and
a first hydrolysis step, wherein said solid matrix is contacted with a second supercritical or near-supercritical fluid to produce a second liquid fraction (including soluble sugars and soluble lignin) and a insoluble lignin-containing fraction;
wherein said second supercritical or near-critical fluid comprises water and, optionally, $CO_2$;
wherein said second supercritical or near-critical fluid is substantially free of $C_1$-$C_5$ alcohols;
a second hydrolysis step wherein said second liquid fraction is contacted with a third near-critical or sub-critical fluid to produce a third liquid fraction comprising glucose monomers;
wherein said third near-critical or sub-critical fluid comprises water and, optionally, acid.

In yet another embodiment, the invention is directed to methods for the continuous treatment of biomass, comprising:
a pretreatment step, wherein said biomass is contacted with a first supercritical, near-critical, or sub-critical fluid to form a solid matrix and a first liquid fraction;
wherein said first supercritical, near-critical, or sub-critical fluid comprises water and, optionally, $CO_2$; and
wherein said first supercritical, near-critical, or sub-critical fluid is substantially free of $C_1$-$C_5$ alcohol;
a hydrolysis step;
wherein said solid matrix is contacted with a second supercritical or near-supercritical fluid to produce a second liquid fraction (including soluble sugars and soluble lignin, if present) and a insoluble lignin-containing fraction;
wherein said second supercritical or near-critical fluid comprises water and, optionally, $CO_2$; and
wherein said second supercritical or near-critical fluid is substantially free of $C_1$-$C_5$ alcohols; and
a xylo-oligosaccharide hydrolysis step, wherein said first liquid fraction is contacted with a fourth near-critical or sub-critical fluid to produce a fourth liquid fraction comprising xylose monomers.

In another embodiment, the present invention is directed to methods for the continuous treatment of biomass, comprising:
a pretreatment step, wherein said biomass is contacted with a first supercritical, near-critical, or sub-critical fluid to form a pretreated slurry comprising a solid matrix and a first liquid fraction comprising xylo-oligosaccharides;
a first separation step, wherein said solid matrix and said first liquid fraction are separated;
a first hydrolysis step, wherein said solid matrix is contacted with a second supercritical or near-critical fluid to form a insoluble lignin-containing fraction and a second liquid fraction comprising cello-oligosaccharides;
a second separation step, wherein said insoluble lignin-containing fraction and said second liquid fraction are separated; and
a second hydrolysis step, wherein said second liquid fraction is contacted with a third near-critical or sub-critical fluid to form a product comprising glucose monomers; and
optionally, a third hydrolysis step, wherein said first liquid fraction is contacted with a fourth near-critical or sub-critical fluid to form a second product comprising xylose monomers.

In yet other embodiments, the invention is directed to methods of increasing the level of xylose produced from biomass, comprising:

fractionating said biomass to form:
 a solid fraction comprising:
  cellulose; and
  insoluble lignin; and
 a first liquid fraction at a first temperature and at a first pressure comprising:
  a soluble $C_5$ saccharide selected from the group consisting of xylo-oligosaccharides, xylose, and mixtures thereof;
separating said solid fraction from said first liquid fraction at a second pressure;
 wherein said first pressure and said second pressure are substantially the same;
 adding to said first liquid fraction an aqueous acid to increase the level of said soluble $C_5$ saccharide in said liquid fraction to form a second liquid fraction at a second temperature; and
 optionally, hydrolyzing said second liquid fraction to form xylose.

In another embodiment, the invention is directed apparatus adapted for continuously converting biomass comprising a pretreatment reactor and a hydrolysis reactor associated with said pretreatment reactor.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
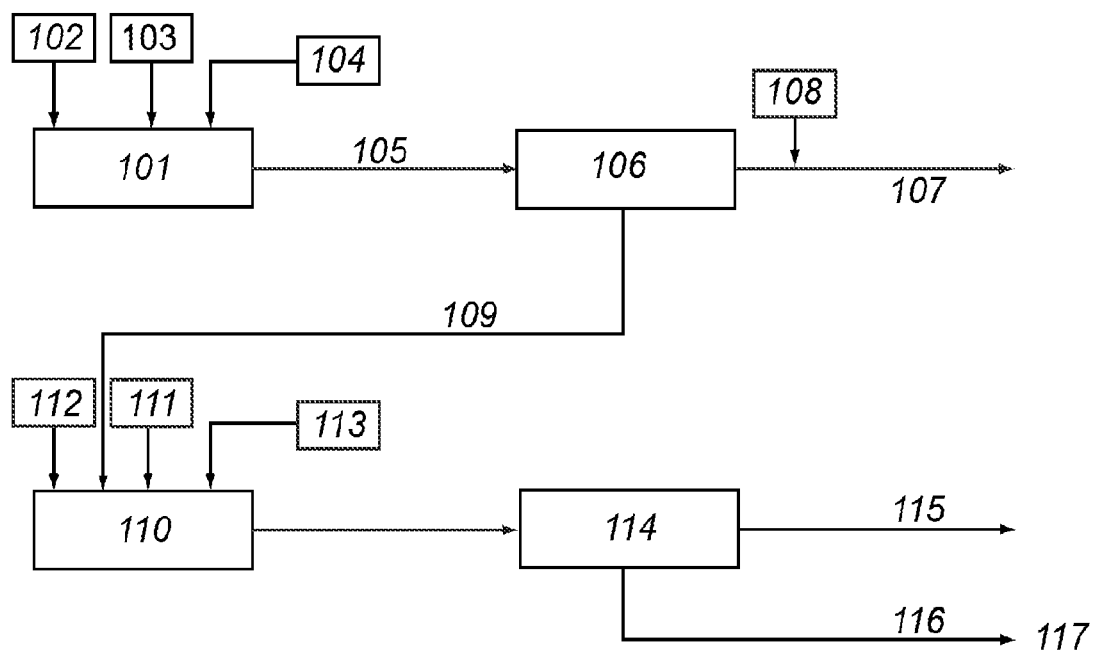
FIG. 1 is a block diagram showing one embodiment of the method of the present invention.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, the term "substantial free of" refers to a composition having less than about 1% by weight, preferably less than about 0.5% by weight, and more preferably less than about 0.1% by weight, based on the total weight of the composition, of the stated material.

Biomass

Biomass is a renewable energy source generally comprising carbon-based biological material derived from recently-living organisms. The organisms may have been plants, animals, fungi, etc. Examples of biomass include without limitation wood, municipal solid waste, manufacturing waste, food waste, black liquor (a byproduct of wood pulping processes), etc. Fossil fuels are generally not considered biomass even though ultimately derived from carbon-based biological material. The term "biomass" as used herein does not include fossil fuel sources.

Biomass can be processed to yield many different chemicals. Generally, biomass can be converted using thermal processes, chemical processes, enzymatic processes, or combinations thereof.

Supercritical, Sub-Critical, and Near-Critical Fluids

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar. Carbon dioxide has a critical point of about 31° C. and about 72.9 atmospheres (about 1072 psig). Ethanol has a critical point of about 243° C. and about 63 atmospheres. Methanol has a critical point of about 239° C. (512.8 K) and about 1174.0 psia (80.9 bar). The critical point for other alcohols can be ascertained from the literature or experimentally.

Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. but less than subcritical and at pressures such that water is in a liquid state As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "$C_1$-$C_5$ alcohol" indicates an alcohol comprising 1 to 5 carbon atoms. Examples of $C_1$-$C_5$ alcohols include, but are not limited to, methanol, ethanol, n-propanol, isopropanol, n-butanol, s-butanol, t-butanol, i-butanol, n-pentanol, 2-pentanol, 3-pentanol, 2-methyl-1-butanol, 2-methyl-2-butanol, 3-methyl-1-butanol, 3-methyl-2-butanol, and 2,2-dimethyl-1-propanol. Mixtures of one or more of these alcohols may be used.

As used herein, "solid matrix" indicates a composition comprising a solid or particulate component.

As used herein, "liquid fraction" indicates a liquid comprising at least one component of which is a product of a reaction or treatment step. For example and without limitation, a liquid fraction after a hydrolysis step may include a product of the hydrolysis step with unreacted components and/or one or more additional products or by-products of the hydrolysis step and/or one or more products of a prior treatment step.

As used herein, "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "resides" indicates the length of time which a given portion or bolus of material is within a reaction zone or reactor vessel. The "residence time," as used herein, including the examples and data, are reported at ambient conditions and are not necessarily actual time elapsed.

FIG. 1 shows a schematic of one embodiment of a method of the invention of converting lignocellulosic biomass 102 to xylose (solution form) 107, glucose (solution form 115), and lignin (solid form) 116. Lignocellulosic biomass 102 is pretreated in a pretreatment reactor 101 using hot compressed water (HCW) 103 (where the hot compressed water is under sub-critical conditions) and, optionally, supercritical $CO_2$ 104 to hydrolyze hemicellulose to hemicellulosic sugars, e.g., xylose and xylo-oligosaccharides. The resultant slurry 105 is subjected to solid/liquid (S/L) separation 106; the liquid phase contains hemicellulosic sugars and the solid phase contains mostly glucan and lignin. Optionally, acid 108, preferably, an inorganic acid (such as sulfuric acid), may be added separately or as part of quenching fluid, not shown. The yields of hemicellulosic sugars in the liquor and of glucan and lignin in the solid phase are typically ≥80%, ≥90%, and ≥90% (of theoretical), respectively. This solid matrix 109 is mixed with water, and optionally preheated, then subjected to hydrolysis in a hydrolysis reactor 110 using supercritical and near-critical fluids. Supercritical water (SCW) 111 and supercritical $CO_2$ 112 (and optionally acid 113) act upon glucan to selectively hydrolyze it while majority of the lignin stays insoluble. After solid/liquid separation 114, liquid phase containing hexose sugars 115 and solid phase containing mostly lignin 116 are obtained. Optionally, an acid 113, preferably an inorganic acid (such as sulfuric acid), can be added as well that enhances cellulose hydrolysis while retarding lignin solubilization. The lignin serves as fuel 117 (such as used in a boiler, not shown) whereas hexose and pentose sugars are feedstocks for fermentations and in deriving high-value intermediates and chemicals.

Pretreatment of Biomass

In one embodiment of a method of the present invention, biomass is subjected to continuous treatment comprising a pretreatment step, wherein said biomass is contacted with a first supercritical, near-critical, or sub-critical fluid to form a solid matrix and a first liquid fraction. In another embodiment, the supercritical or near-critical fluid comprises water and, optionally, carbon dioxide, and is substantially free of $C_1$-$C_5$ alcohols. In another embodiment, the supercritical or near-critical fluid comprises water and carbon dioxide. In embodiments of the present invention where the supercritical or near-critical fluid comprises carbon dioxide, the amount of carbon dioxide present may be less than about 10%, less than about 9%, less than about 8%, less than about 7%, less than about 6%, less than about 5%, less than about 4%, less than about 3%, less than about 2%, or less than about 1%. In another embodiment, the supercritical or near-critical fluid does not include carbon dioxide. In another embodiment, the supercritical or near-critical fluid does not include an alcohol.

In another embodiment, the pretreatment step occurs at a temperature and pressure above the critical point of at least one component of a fluid. In another embodiment, the pretreatment step occurs at a temperature and pressure above the critical point of all components of the fluid. In another embodiment, the pretreatment step occurs at a temperature from about 180° C. to about 260° C., for example, from about 185° C. to about 255° C., from about 190° C. to about 250° C., from about 195° C. to about 245° C., from about 200° C. to about 240° C., from about 205° C. to about 235° C., from about 210° C. to about 230° C., from about 215° C. to about 225° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., or about 260° C.

In another embodiment, the pretreatment step occurs at a pressure from about 50 bar to about 110 bar, for example, from about 50 bar to about 110 bar, from about 60 bar to about 105 bar, from about 70 bar to about 100 bar, from about 80 bar to about 95 bar, about 50 bar, about 55 bar, about 60 bar, about 65 bar, about 70 bar, about 75 bar, about 80 bar, about 85 bar, about 90 bar, about 95 bar, about 100 bar, about 105 bar, or about 110 bar.

In another embodiment, the pretreatment step occurs at a temperature from about 180° C. to about 260° C. and at a pressure from about 50 bar to about 110 bar. In another embodiment, the pretreatment step occurs at a temperature from about 230° C. to about 240° C. and at a pressure of about 50 bar.

In another embodiment, the biomass resides in the pretreatment step for about 1 to about 5 minutes, for example, about 1 minute, about 1.1 minutes, about 1.2 minutes, about 1.3 minutes, about 1.4 minutes, about 1.5 minutes, about 1.6 minutes, about 1.7 minutes, about 1.8 minutes, about 1.9 minutes, about 2 minutes 2.1 minutes, about 2.2 minutes, about 2.3 minutes, about 2.4 minutes, about 2.5 minutes, about 2.6 minutes, about 2.7 minutes, about 2.8 minutes, about 2.9 minutes, about 3 minutes, about 3.1 minutes, about 3.2 minutes, about 3.3 minutes, about 3.4 minutes, about 3.5 minutes, about 3.6 minutes, about 3.7 minutes, about 3.8 minutes, about 3.9 minutes, about 4 minutes, about 4.1 minutes, about 4.2 minutes, about 4.3 minutes, about 4.4 minutes, about 4.5 minutes, about 4.6 minutes, about 4.7 minutes, about 4.8 minutes, about 4.9 minutes, or about 5 minutes.

In one embodiment, the products of the pretreatment step are cooled after completion of the pretreatment step. Cooling may be accomplished by any means known in the art including, without limitation, direct cooling, indirect cooling, passive cooling, etc. The term "direct cooling" as used herein indicates that a cooling fluid is contacted or mixed with the products of the pretreatment step, wherein the cooling fluid has a lower temperature than the products of the pretreatment step. For example and without limitation, direct cooling may be accomplished by contacting the products of the pretreatment step with a cooling fluid comprising water, wherein the cooling fluid has a lower temperature than the products of the pretreatment step. In direct cooling embodiments, the cooling fluid is in direct contact with and may mix with the products of the pretreatment step. In contrast, the term "indirect cooling" as used herein indicates that cooling is accomplished by means wherein the products of the pretreatment step are not contacted with or mixed with a cooling fluid. For example and without limitation, indirect cooling may be accomplished by cooling at least a portion of the vessel in which the products of the pretreatment step are located. In indirect cooling embodiments, the products of the pretreatment step are not directly in contact with, and therefore do not mix with, the cooling fluid. The term "passive cooling" as used herein indicates that the temperature of the pretreated biomass is reduced without contacting the pretreated biomass with a cooling fluid. For example and without limitation, pretreated biomass may be passively cooled by storing the pretreated biomass in a holding tank or reservoir for a period of time during which the temperature of the pretreated biomass lowers in response to ambient temperature conditions. Alternatively, pretreated biomass may be passively cooled by passing the pretreated biomass through a tube or other conveying means en route to a second treatment reactor wherein the tube or other conveying means is not cooled by contact with a cooling fluid. The term "cooling fluid" as used herein includes solids, liquids, gases, and combinations thereof. In either direct or indirect cooling embodiments, cooling may be accomplished by means other than use of a cooling fluid, for example by induction. The term "heat exchange" as used herein includes direct cooling, indirect cooling, passive cooling, and combinations thereof.

Solid-Liquid Separation of Pretreated Biomass

In one embodiment, the pretreated biomass comprises a solid matrix and a liquid fraction. The solid fraction may comprise, for example, cellulose and lignin, while the liquid fraction may comprise, for example, xylo-oligosaccharides. In one embodiment, the solid fraction and the liquid fraction are separated. Separation may occur, for example, by filtration, centrifugation, extrusion, etc.

In one embodiment, the solid fraction and liquid fraction are separated by extrusion. This is shown generally in FIG. 6, where a motor 602 is used to drive extruder screws 601 within an extruder barrel 603 to move slurry from pretreatment or cellulose hydrolysis 604 within the extruder. A dynamic plug 605 of extruded material is formed, creating a low pressure zone prior to the plug and a high pressure zone beyond the plug in the extruder barrel. The liquid fraction is squeezed from the wet extruded material 606 prior to the dynamic plug 605. The solid fraction 607 (for example, at ~45% solids) exits through the extruder. The pitch of a screw is defined as the distance between one crest of the screw thread to the next crest of the screw thread. The term "variable-pitch screw" indicates a screw with threads having more than one pitch along the axis. Thus according to one embodiment, an extruder for separating the solid matrix and the liquid fraction comprises a plurality of variable-pitch screws. In one embodiment, the screw(s) of the extruder are driven by one or more motors.

Hydrolysis of Pretreated Solid Matrix

In one embodiment, the solid matrix formed during pretreatment is subjected to further processing. In one embodiment, the solid matrix is contacted with a second supercritical or near-critical fluid. In a related embodiment, the second supercritical or near-critical fluid is the same as the first supercritical, near-critical, or sub-critical fluid used during the pretreatment step. In another embodiment the second supercritical or near-critical fluid is different from the first supercritical, near-critical, or sub-critical fluid used during the pretreatment step. For example and without limitation, the second supercritical or near-critical fluid may comprise one or more additional components or one or more fewer components compared to the first supercritical, near-critical, or sub-critical fluid. Alternatively, the second supercritical or near-critical fluid may comprise the same components as the first supercritical, near-critical, or sub-critical fluid, but in a ratio different than that of the first supercritical, near-critical, or sub-critical fluid. In another embodiment, the second supercritical or near-critical fluid has the same components as the first supercritical, near-critical, or sub-critical fluid, optionally in the same ratios, but is used at a temperature and/or pressure different than the first supercritical, near-critical, or sub-critical fluid. In a related embodiment, the temperature and pressure of the second supercritical or near-critical fluid differs from that of the first supercritical, near-critical, or sub-critical fluid such that one or more components of the second supercritical or near-critical fluid are in a different state than they are in when in the first supercritical, near-critical, or sub-critical fluid. For example and without limitation, the first and second supercritical or near-critical fluids may each comprise water and carbon dioxide, but the temperature and pressure of the first supercritical, near-critical, or sub-critical fluid is such that both components are in the supercritical state, while the temperature and pressure of the second supercritical or near-critical fluid is such that the water is in a near-critical or subcritical state.

In one embodiment, the second supercritical or near-critical fluid comprises water and, optionally, carbon dioxide, and is substantially free of $C_1$-$C_5$ alcohols. In another embodiment, the second supercritical or near-critical fluid comprises water and carbon dioxide. In embodiments of the present invention where the second supercritical or near-critical fluid comprises carbon dioxide, the amount of carbon dioxide present may be less than about 10%, less than about 9%, less than about 8%, less than about 7%, less than about 6%, less than about 5%, less than about 4%, less than about 3%, less than about 2%, or less than about 1%. In another embodiment, the second supercritical or near-critical fluid does not include carbon dioxide.

In one embodiment, the solid matrix has a residence time in the hydrolysis step of about 1 second to about 45 seconds. In another embodiment, the solid matrix has a residence time in the hydrolysis step of about 1 second to about 30 seconds. In another embodiment, the solid matrix has a residence time in the hydrolysis step of about 1 second to about 20 seconds. In another embodiment, the solid matrix has a residence time in the hydrolysis step of about 1 second to about 15 seconds. In another embodiment, the solid matrix has a residence time in the hydrolysis step of about 1 second to about 10 seconds. In another embodiment, the solid matrix has a residence time in the hydrolysis step of about 1 second to about 5 seconds. In another embodiment, the solid matrix has a residence time in the hydrolysis step of about 1 second to about 4 seconds. In another embodiment, the solid matrix has a residence time in the hydrolysis step of about 1 second to about 3 seconds. In another embodiment, the solid matrix has a residence time in the hydrolysis step of about 1 second to about 2 seconds. In another embodiment, the solid matrix has a residence time in the hydrolysis step of less than about 1 second. In another embodiment, the solid matrix has a residence time in the hydrolysis step of about 1 second, about 1.1 seconds, about 1.2 seconds, about 1.3 seconds, about 1.4 seconds, about 1.5 seconds, about 1.6 seconds, about 1.7 seconds, about 1.8 seconds, about 1.9 seconds, or about 2 seconds.

In one embodiment, the hydrolysis step occurs at a temperature above the critical temperature of one or more components of the second supercritical or near-critical fluid. In another embodiment, the hydrolysis step occurs at a temperature of about 275° C. to about 450° C. In another embodiment, the hydrolysis step occurs at a temperature of about 300° C. to about 440° C. In another embodiment, the hydrolysis step occurs at a temperature of about 320° C. to about 420° C. In another embodiment, the hydrolysis step occurs at a temperature of about 340° C. to about 400° C. In another embodiment, the hydrolysis step occurs at a temperature of about 350° C. to about 390° C. In another embodiment, the hydrolysis step occurs at a temperature of about 360° C. to about 380° C. In another embodiment, the hydrolysis step occurs at a temperature of about 370° C. to about 380° C. In another embodiment, the hydrolysis step occurs at a temperature of about 377° C.

In one embodiment, the hydrolysis step occurs at a pressure above the critical pressure of one or more components of the second supercritical or near-critical fluid. In another embodiment, the hydrolysis step occurs at a pressure of about 200 bar to about 250 bar. In another embodiment, the hydrolysis step occurs at a pressure of about 210 bar to about 240 bar. In another embodiment, the hydrolysis step occurs at a pressure of about 220 bar to about 230 bar. In another embodiment, the hydrolysis step occurs at a pressure of about 200 bar, about 205 bar, about 210 bar, about 215 bar, about 220 bar, about 225 bar, about 230 bar, about 235 bar, about 240 bar, about 245 bar, or about 250 bar.

In one embodiment, the hydrolysis step occurs at a temperature and pressure above the critical temperature and critical pressure, respectively, of one or more components of the second supercritical or near-critical fluid. In another embodiment, the hydrolysis step occurs at a temperature of about 300° C. to about 440° C. and a pressure of about 200 bar to about 250 bar.

In one embodiment, the solid matrix is fed into a hydrolysis or treatment reactor by an extruder. In a related embodiment, the extruder comprises one to a plurality of screws. In a related embodiment, the extruder consists of two screws (a "twin-screw extruder"). In another embodiment, the extruder comprises a plurality of variable-pitch screws.

Figure 8:
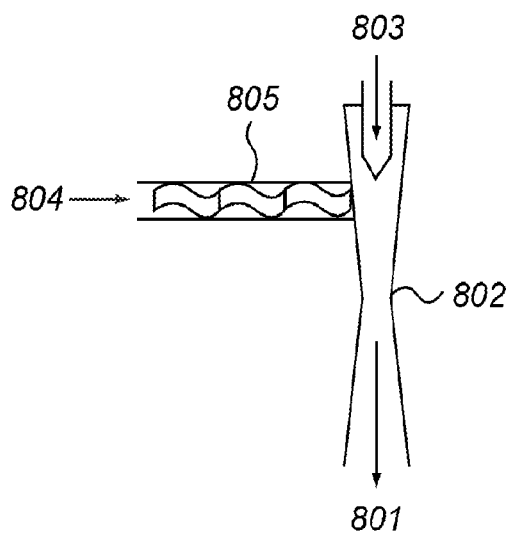
FIG. 8 shows one example in schematic form of incorporation of a solid matrix produced by pretreatment of biomass into a treatment reactor using an extruder and an eductor according to one embodiment of the present invention.

In one embodiment, the solid matrix is fed into a hydrolysis reactor (not shown) by an eductor associated with the hydrolysis reactor. In one embodiment, steam 803 is used to propel or draw the solid matrix 801 through the eductor 802 and into the hydrolysis reactor (not shown), as shown, for example, in FIG. 8, using an extruder 805 to move the solids feed 804 into the eductor 802.

Figure 9:
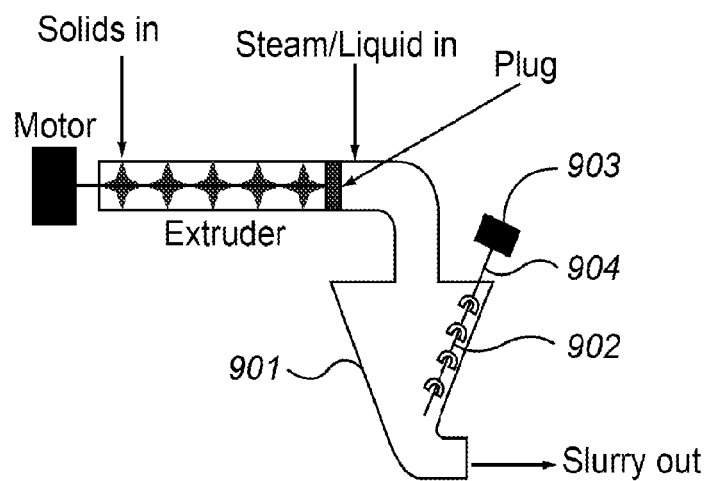
FIG. 9 depicts a conical treatment reactor according to one embodiment of the present invention.
Figure 10:
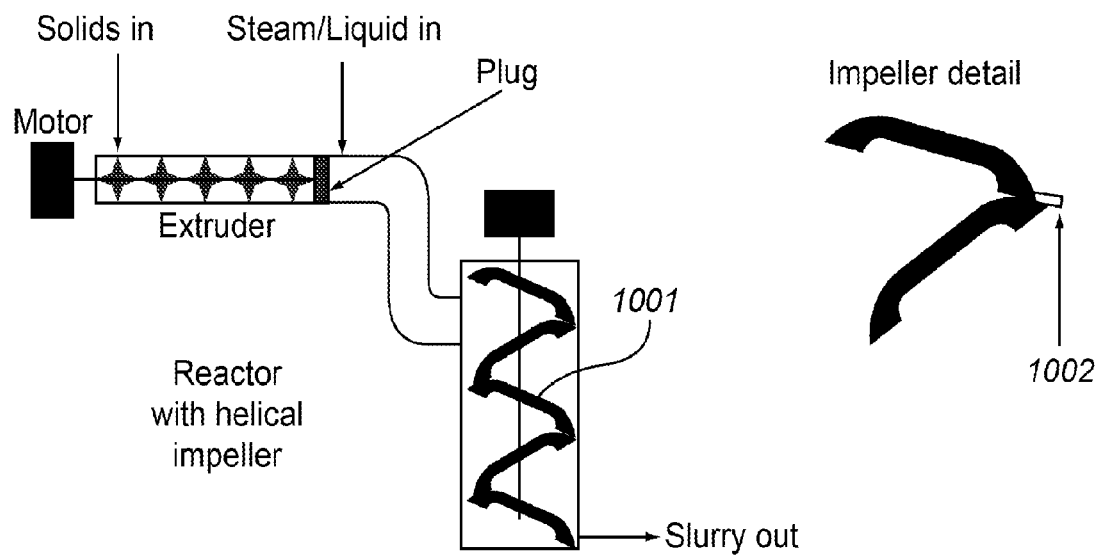
FIG. 10 depicts a continuously stirred treatment reactor according to one embodiment of the present invention.
Figure 11:
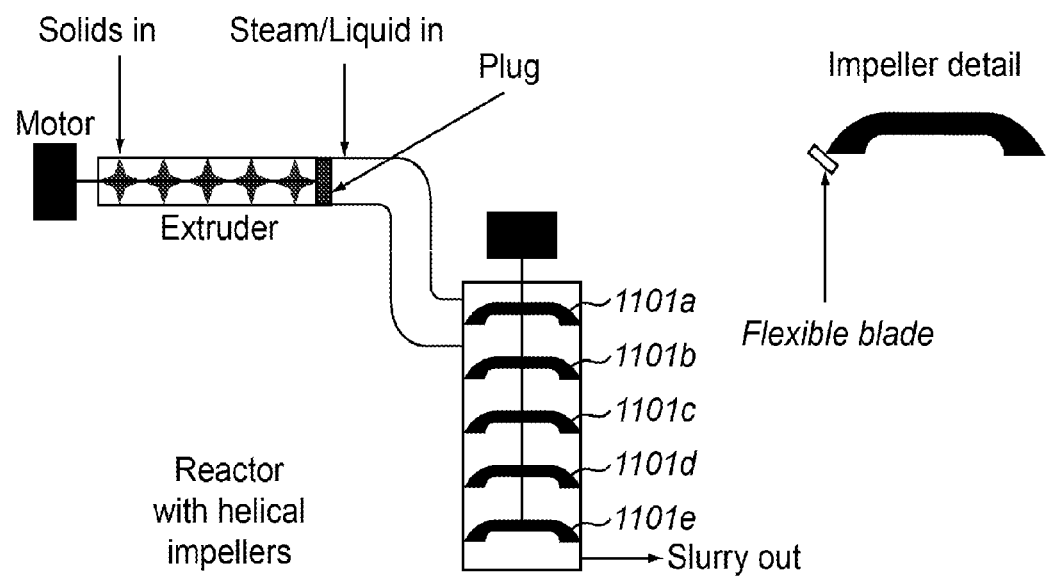
FIG. 11 depicts an alternative embodiment of a continuously stirred treatment reactor according to one embodiment of the present invention.

In one embodiment, hydrolysis occurs in a hydrolysis reactor. In one embodiment, the hydrolysis reactor comprises a conical reactor 901, such as shown in FIG. 9. In another embodiment the hydrolysis reactor comprises a tank reactor. In one embodiment, the contents of the hydrolysis reactor are stirred during hydrolysis. In a related embodiment, the hydrolysis reactor contents are stirred continuously. The term "stirred continuously" or alternatively "continuously stirred" as used herein indicates that the contents of the reactor are agitated, mixed, etc. during most of the hydrolysis step, during substantially all of the hydrolysis step, or during all of the hydrolysis step. Brief or intermittent periods of time during which the reactor contents are not stirred fall within the meaning of "stirred continuously" and "continuously stirred" as used herein. Agitation or stirring may be accomplished by any means known in the art including, without limitation, mechanical agitation or stirring, by vibrations, or by non-uniform injection of the supercritical fluid into the hydrolysis reactor. In one embodiment, stirring is accomplished by an impeller associated with a motor 903. In a related embodiment, the impeller is associated with a shaft 904 which in turn is associated with a motor 903. In a related embodiment, the impeller is helically associated with the shaft. In another embodiment, the impeller is circumferentially associated with the shaft. In a related embodiment, the impeller comprises a helical impeller 1001, as shown, for example, in FIG. 10. In another embodiment, the impeller comprises flexible blades 1002. In another embodiment, the impeller comprises a plurality of blades, as shown, for example, in FIG. 11 with impeller blades 1101a, 1101b, 1101c, 1101d, and 1101e. In another embodiment, the impeller comprises a plurality of helical blades.

Figure 6:
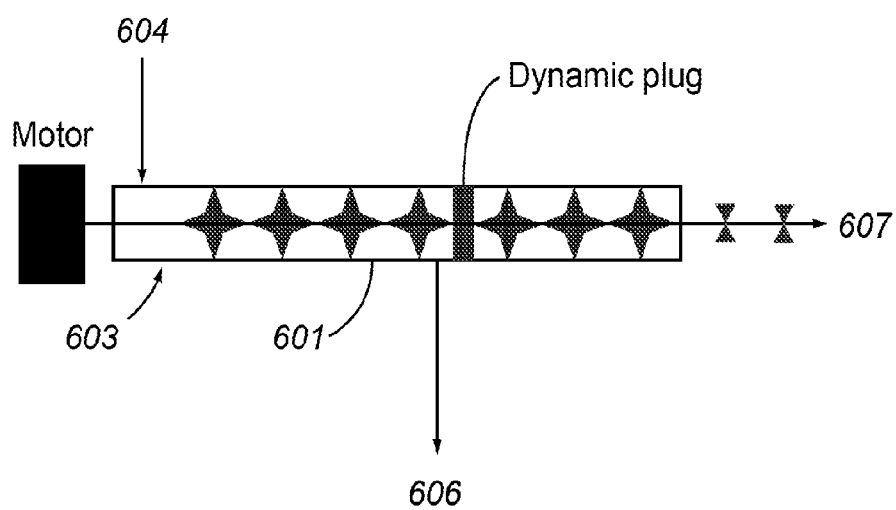
FIG. 6 depicts a schematic representation of solid-liquid separation achieved by use of an extruder according to one embodiment of the present invention.

In one embodiment, the hydrolysis reactor comprises a tube (i.e., a tubular hydrolysis reactor). In a related embodiment, the tubular hydrolysis reactor is an extruder. In a related embodiment, the extruder comprises a screw. In another embodiment, the extruder comprises a plurality of screws. In another embodiment, the one or more screws of the extruder are variable pitch screws. In another embodiment, the one or more screws of the extruder are associated with one or more motors. In an embodiment wherein the extruder comprises two or more screws, said screws co-rotate. In an embodiment wherein the extruder includes two screws (a "twin-screw extruder"), said screws 601 co-rotate, as shown in FIG. 6. In an embodiment in which the extruder is a twin-screw extruder, said screws counter-rotate.

In one embodiment, the solid matrix is maintained at a temperature of at least about 175° C., at least about 180° C., at least about 185° C., at least about 190° C., at least about 195° C., or at least about 200° C. from the beginning of the pretreatment step through at least the end of the hydrolysis step. The term "maintained at a temperature of at least" as used herein indicates that the temperature of the solid matrix does not drop significantly below the specified temperature.

In one embodiment, hydrolysis of the solid matrix according to a process of the present invention produces at least a lignin-insoluble fraction and a second liquid fraction (including soluble sugars and soluble lignin, if present). In one embodiment, the second liquid fraction comprises glucose, cello-oligosaccaharides, and soluble lignin, if present. In one embodiment, the lignin-insoluble fraction comprises insoluble lignin. In another embodiment, the second liquid fraction comprises glucose and cello-oligosaccharides and the lignin-insoluble fraction comprises insoluble lignin.

In one embodiment, at least one of the lignin-insoluble fraction and the second liquid fraction are cooled after the hydrolysis step. In one embodiment, cooling occurs before the lignin-insoluble fraction and the second liquid fraction are separated. In another embodiment, cooling occurs after the lignin-insoluble fraction and the second liquid fraction are separated. In another embodiment, at least a portion of the cooling step occurs concomitantly with separation of the lignin-insoluble fraction and the second liquid fraction. In one embodiment, one or more of the lignin-insoluble fraction and the second liquid fraction are cooled to a temperature of about 180° C. to about 240° C., about 185° C. to about 235° C., about 190° C. to about 230° C., about 195° C. to about 225° C., about 200° C. to about 220° C., about 205° C. to about 215° C., about 180° C., about 185° C., about 190° C., about 195° C., about 200° C., about 205° C., about 210° C., about 215° C., about 220° C., about 225° C., about 230° C., about 235° C., or about 240° C.

In one embodiment, one or more of the lignin-insoluble fraction and the second liquid fraction are flash cooled. In another embodiment, one or more of the lignin-insoluble fraction and the second liquid fraction are flash cooled to a temperature of about 20° C. to about 90° C., about 25° C. to about 85° C., about 30° C. to about 80° C., about 35° C. to about 75° C., about 40° C. to about 70° C., about 45° C. to about 65° C., about 50° C. to about 60° C., about 20° C., about 25° C., about 30° C., about 35° C., about 40° C., about 45° C., about 50° C., about 55° C., about 60° C., about 65° C., about 70° C., about 75° C., about 80° C., about 85° C., or about 90° C. In one embodiment, one or more of the lignin-insoluble fraction and the second liquid fraction are flash cooled after the hydrolysis step but before any separation step. In a related embodiment, one or more of the lignin-insoluble fraction and the second liquid fraction are flash cooled without any initial cooling after hydrolysis. In another embodiment, one or more of the lignin-insoluble fraction and the second liquid fraction are flash cooled after first separating the lignin-insoluble fraction from the second liquid fraction. In another embodiment, at least a portion of the flash cooling step occurs concomitantly with a separation step. In another embodiment, one or more of the lignin-insoluble fraction and the second liquid fraction are flash cooled after first cooling to a temperature of about 180° C. to about 240° C., about 185° C. to about 235° C., about 190° C. to about 230° C., about 195° C. to about 225° C., about 200° C. to about 220° C., about 205° C. to about 215° C., about 180° C., about 185° C., about 190° C., about 195° C., about 200° C., about 205° C., about 210° C., about 215° C., about 220° C., about 225° C., about 230° C., about 235° C., or about 240° C.

Cooling and/or flash cooling may be accomplished by any means known in the art including, without limitation, drawing or removing water from the mixture, rapidly decreasing the pressure exerted on the mixture, contacting the mixture with a relatively cooler gas, liquid or other material, etc.

Separation of Hydrolyzed Mixture

In one embodiment, the lignin-insoluble fraction and second liquid fraction are separated by extrusion. In a related embodiment, extrusion occurs in an extruder. In a related embodiment, an extruder used to separate the lignin-insoluble fraction and second liquid fraction comprises one to a plurality of screws. In a related embodiment, the extruder includes two screws. This is shown generally in FIG. 6, where a motor 602 is used to drive extruder screws 601 within an extruder barrel 603 to move slurry from pretreatment or cellulose hydrolysis 604 within the extruder. A dynamic plug 605 of extruded material is formed, creating a low pressure zone prior to the plug and a high pressure zone beyond the plug in the extruder barrel. The liquid fraction is squeezed from the wet extruded material 606 prior to the dynamic plug 605. The solid fraction 606 (for example, at ~45% solids) exits through the extruder. In one embodiment, an extruder for separating the solid matrix and the liquid fraction may comprise one to a plurality of variable-pitch screws. In one embodiment, the screw(s) of the extruder are rotatably associated with, or driven by, one or more motors.

In one embodiment, the temperature of the pretreated biomass is maintained above about 185° C. through the hydrolysis step, and then the temperature is reduced to about 220° C. before flash cooling the hydrolyzed slurry by quickly reducing the pressure to about atmospheric pressure. In a related embodiment, separation of the lignin-insoluble fraction from the second liquid fraction is achieved by skimming or filtration. In a related embodiment, the temperature of the hydrolyzed slurry is reduced such that the lignin precipitates. In a related embodiment, lignin precipitates without the addition of a precipitation or flocculating agent. In another embodiment, the pressure exerted on the products of the hydrolysis step is reduced to about 105 kPa or less, or about 101.325 kPa or less after the hydrolysis step.

Hydrolysis of Cello-Oligosaccharides

One embodiment includes a second hydrolysis step wherein the second liquid fraction is contacted with a third near-critical or sub-critical fluid to produce a third liquid fraction comprising glucose monomers.

In one embodiment the second hydrolysis step occurs at a temperature that is greater than the critical temperature of at least one component of the fluid. In another embodiment, the second hydrolysis step occurs at a temperature of about 220° C. to about 320° C., about 230° C. to about 310° C., about 240° C. to about 300° C., about 250° C. to about 290° C., about 260° C. to about 280° C., about 220° C., about 230° C., about 240° C., about 250° C., about 260° C., about 270° C., about 280° C., about 290° C., about 300° C., about 310° C., or about 320° C.

In one embodiment, the second hydrolysis step occurs at a pressure greater than the critical pressure of at least one component of the fluid. In another embodiment, the second hydrolysis step occurs at a pressure of about 30 bar to about 90 bar, about 35 bar to about 85 bar, about 40 bar to about 80 bar, about 45 bar to about 75 bar, about 50 bar to about 70 bar, about 55 bar to about 65 bar, about 30 bar, about 35 bar, about 40 bar, about 45 bar, about 50 bar, about 55 bar, about 60 bar, about 65 bar, about 70 bar, about 75 bar, about 80 bar, about 85 bar, or about 90 bar.

In one embodiment, the second hydrolysis step occurs at a temperature and pressure greater than the critical temperature and critical pressure, respectively, of one or more components of the fluid. In another embodiment, the second hydrolysis step occurs at a temperature of about 220° C. to about 320° C., about 230° C. to about 310° C., about 240° C. to about 300° C., about 250° C. to about 290° C., about 260° C. to about 280° C., about 220° C., about 230° C., about 240° C., about 250° C., about 260° C., about 270° C., about 280° C., about 290° C., about 300° C., about 310° C., or about 320° C., and a pressure of about 30 bar to about 90 bar, about 35 bar to about 85 bar, about 40 bar to about 80 bar, about 45 bar to about 75 bar, about 50 bar to about 70 bar, about 55 bar to about 65 bar, about 30 bar, about 35 bar, about 40 bar, about 45 bar, about 50 bar, about 55 bar, about 60 bar, about 65 bar, about 70 bar, about 75 bar, about 80 bar, about 85 bar, or about 90 bar.

In one embodiment, the third near-critical or sub-critical fluid comprises water. In another embodiment, the third near-critical or sub-critical fluid further comprises acid (either an inorganic acid or an organic acid). In another embodiment, the third near-critical or sub-critical fluid further comprises carbon dioxide. In another embodiment, the third near-critical or sub-critical fluid comprises water and acid. In another embodiment, the third near-critical or sub-critical fluid comprises an alcohol. In another embodiment, the third near-critical or sub-critical fluid does not include an alcohol. In another embodiment, the third near-critical or sub-critical fluid comprises water, carbon dioxide, and an acid.

In embodiments where the third near-critical or sub-critical fluid comprises an acid, the amount of acid may be present in an amount from about 0.1% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%. In another embodiment, the third near-critical or sub-critical fluid comprises a catalytic amount of acid. In embodiments where the third near-critical or sub-critical fluid comprises an acid (either an inorganic acid or an organic acid). Suitable inorganic acids include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. The acid may be selected from the group consisting of hydrofluoric acid, hydrochloric acid, hydrobromic acid, hydroiodic acid, sulfuric acid, sulfonic acid, phosphoric acid, phosphonic acid, nitric acid, nitrous acid, and combinations thereof.

In embodiments where the third near-critical or sub-critical fluid comprises carbon dioxide, the amount of carbon dioxide present may be less than about 10%, less than about 9%, less than about 8%, less than about 7%, less than about 6%, less than about 5%, less than about 4%, less than about 3%, less than about 2%, or less than about 1%, by weight, based on the weight of the third near-critical or sub-critical fluid. In another embodiment, the third near-critical or sub-critical fluid does not include carbon dioxide.

In one embodiment, the second liquid fraction has a residence time in the second hydrolysis step of about 1 second to about 30 seconds, about 1 second to about 25 seconds, about 1 second to about 20 seconds, about 1 second to about 15 seconds, about 1 second to about 10 seconds, about 1 second to about 5 seconds, about 5 seconds to about 30 seconds, about 5 seconds to about 25 seconds, about 5 seconds to about 20 seconds, about 5 seconds to about 15 seconds, about 5 seconds to about 10 seconds, about 1 second, about 1.1 seconds, about 1.2 seconds, about 1.3 seconds, about 1.4 seconds, about 1.5 seconds, about 1.6 seconds, about 1.7 seconds, about 1.8 seconds, about 1.9 seconds, about 2 seconds, about 2.1 seconds, about 2.2 seconds, about 2.3 seconds, about 2.4 seconds, about 2.5 seconds, about 2.6 seconds, about 2.7 seconds, about 2.8 seconds, about 2.9 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, or about 30 seconds.

In one embodiment, the products of the second hydrolysis step are cooled after completion of the hydrolysis step. Cooling may be accomplished by any means known in the art including, without limitation, direct cooling, indirect cooling, passive cooling, etc. The term "direct cooling" as used herein indicates that a cooling fluid is contacted or mixed with the products of the second hydrolysis step, wherein the cooling fluid has a lower temperature than the products of the second hydrolysis step. For example and without limitation, direct cooling may be accomplished by contacting the products of the second hydrolysis step with a cooling fluid comprising water, wherein the cooling fluid has a lower temperature than the products of the second hydrolysis step. In direct cooling embodiments, the cooling fluid is in direct contact with and may mix with the products of the second hydrolysis step. In contrast, the term "indirect cooling" as used herein indicates that cooling is accomplished by means wherein the products of the second hydrolysis step are not contacted with or mixed with a cooling fluid. For example and without limitation, indirect cooling may be accomplished by cooling at least a portion of the vessel in which the products of the second hydrolysis step are located. In indirect cooling embodiments, the products of the second hydrolysis step are not directly in contact with, and therefore do not mix with, the cooling fluid. The term "passive cooling" as used herein indicates that the temperature of the pretreated biomass is reduced without contacting the pretreated biomass with a cooling fluid. For example and without limitation, the products of the second hydrolysis step may be passively cooled by storing the products in a holding tank or reservoir for a period of time during which the temperature of the products lowers in response to ambient temperature conditions. Alternatively, the products of the second hydrolysis step may be passively cooled by passing the products through a tube or other conveying means wherein the tube or other conveying means is not cooled by contact with a cooling fluid. The term "cooling fluid" as used herein includes solids, liquids, gases, and combinations thereof. In either direct or indirect cooling embodiments, cooling may be accomplished by means other than use of a cooling fluid, for example by induction. The term "heat exchange" as used herein includes direct cooling, indirect cooling, and combinations thereof.

In one embodiment, the third liquid fraction comprises glucose. In one embodiment, the third liquid fraction comprises glycolaldehyde. In a related embodiment, glycolaldehyde is present in the third liquid fraction in an amount of at least about 5%, at least about 10%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the theoretical maximum yield of glycolaldehyde. In one embodiment, glycolaldehyde is present in the third liquid fraction in an amount less than the amount of glucose present in the third liquid fraction. In one embodiment, glycolaldehyde is present in the third liquid fraction in an amount greater than the amount of glucose present in the third liquid fraction Hydrolysis of Xylo-oligosaccharides In one embodiment, the first liquid fraction formed by pretreatment of biomass is contacted with a fourth near-critical or sub-critical fluid to produce a fourth liquid fraction comprising xylose monomers.

In one embodiment, the fourth near-critical or sub-critical fluid comprises water. In another embodiment, the fourth near-critical or sub-critical fluid comprises carbon dioxide. In another embodiment, the fourth near-critical or sub-critical fluid comprises water and carbon dioxide. In another embodiment, the fourth near-critical or sub-critical fluid comprises an alcohol. In another embodiment, the fourth near-critical or sub-critical fluid does not include an alcohol. In another embodiment, the fourth near-critical or sub-critical fluid comprises an acid. In another embodiment, the fourth near-critical or sub-critical fluid comprises water, carbon dioxide, and an acid.

In embodiments where the fourth near-critical or sub-critical fluid comprises carbon dioxide, the amount of carbon dioxide present may be less than about 10%, less than about 9%, less than about 8%, less than about 7%, less than about 6%, less than about 5%, less than about 4%, less than about 3%, less than about 2%, or less than about 1%. In another embodiment, the fourth near-critical or sub-critical fluid does not include carbon dioxide.

In embodiments where the fourth near-critical or sub-critical fluid comprises an acid, the amount of acid may be present in an amount from about 0.1% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%. In another embodiment, the fourth near-critical or sub-critical fluid comprises a catalytic amount of acid. In embodiments where the fourth near-critical or sub-critical fluid comprises an acid (either an inorganic acid or an organic acid). Suitable inorganic acids include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. The acid may be selected from the group consisting of hydrofluoric acid, hydrochloric acid, hydrobromic acid, hydroiodic acid, sulfuric acid, sulfonic acid, phosphoric acid, phosphonic acid, nitric acid, nitrous acid, and combinations thereof.

In one embodiment, the first liquid fraction has a residence time in the xylo-oligosaccharide hydrolysis step of about 1 second to about 30 seconds, about 1 second to about 25 seconds, about 1 second to about 20 seconds, about 1 second to about 15 seconds, about 1 second to about 10 seconds, about 1 second to about 5 seconds, about 5 seconds to about 30 seconds, about 2 seconds to about 25 seconds, about 5 seconds to about 25 seconds, about 5 seconds to about 20 seconds, about 5 seconds to about 15 seconds, about 5 seconds to about 10 seconds, about 10 seconds to about 15 seconds, about 1 second, about 1.1 seconds, about 1.2 seconds, about 1.3 seconds, about 1.4 seconds, about 1.5 seconds, about 1.6 seconds, about 1.7 seconds, about 1.8 seconds, about 1.9 seconds, about 2 seconds, about 2.1 seconds, about 2.2 seconds, about 2.3 seconds, about 2.4 seconds, about 2.5 seconds, about 2.6 seconds, about 2.7 seconds, about 2.8 seconds, about 2.9 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, or about 30 seconds.

In one embodiment the xylo-oligosaccharide hydrolysis step occurs at a temperature that is greater than the critical temperature of at least one component of the fourth fluid. In another embodiment, the second hydrolysis step occurs at a temperature of about 220° C. to about 320° C., about 230° C. to about 310° C., about 240° C. to about 300° C., about 250° C. to about 290° C., about 260° C. to about 280° C., about 220° C., about 230° C., about 240° C., about 250° C., about 260° C., about 270° C., about 280° C., about 290° C., about 300° C., about 310° C., or about 320° C.

In one embodiment, the xylo-oligosaccharide hydrolysis step occurs at a pressure greater than the critical pressure of at least one component of the fourth fluid. In another embodiment, the second hydrolysis step occurs at a pressure of about 30 bar to about 90 bar, about 35 bar to about 85 bar, about 40 bar to about 80 bar, about 45 bar to about 75 bar, about 50 bar to about 70 bar, about 55 bar to about 65 bar, about 30 bar, about 35 bar, about 40 bar, about 45 bar, about 50 bar, about 55 bar, about 60 bar, about 65 bar, about 70 bar, about 75 bar, about 80 bar, about 85 bar, or about 90 bar.

In one embodiment, the xylo-oligosaccharide hydrolysis step occurs at a temperature and pressure greater than the critical temperature and critical pressure, respectively, of one or more components of the fourth fluid. In another embodiment, the xylo-oligosaccharide hydrolysis step occurs at a temperature of about 220° C. to about 320° C., about 230° C. to about 310° C., about 240° C. to about 300° C., about 250° C. to about 290° C., about 260° C. to about 280° C., about 220° C., about 230° C., about 240° C., about 250° C., about 260° C., about 270° C., about 280° C., about 290° C., about 300° C., about 310° C., or about 320° C., and a pressure of about 30 bar to about 90 bar, about 35 bar to about 85 bar, about 40 bar to about 80 bar, about 45 bar to about 75 bar, about 50 bar to about 70 bar, about 55 bar to about 65 bar, about 30 bar, about 35 bar, about 40 bar, about 45 bar, about 50 bar, about 55 bar, about 60 bar, about 65 bar, about 70 bar, about 75 bar, about 80 bar, about 85 bar, or about 90 bar.

In one embodiment, the products of the xylo-oligosaccharide hydrolysis step are cooled after completion of the xylo-oligosaccharide hydrolysis step. Cooling may be accomplished by any means known in the art including, without limitation, direct cooling or indirect cooling. The term "direct cooling" as used herein indicates that a cooling fluid is contacted or mixed with the products of the xylo-oligosaccharide hydrolysis step, wherein the cooling fluid has a lower temperature than the products of the xylo-oligosaccharide hydrolysis step. For example and without limitation, direct cooling may be accomplished by contacting the products of the xylo-oligosaccharide hydrolysis step with a cooling fluid comprising water, wherein the cooling fluid has a lower temperature than the products of the xylo-oligosaccharide hydrolysis step. In direct cooling embodiments, the cooling fluid is in direct contact with and may mix with the products of the xylo-oligosaccharide hydrolysis step. In contrast, the term "indirect cooling" as used herein indicates that cooling is accomplished by means wherein the products of the xylo-oligosaccharide hydrolysis step are not contacted with or mixed with a cooling fluid. For example and without limitation, indirect cooling may be accomplished by cooling at least a portion of the vessel in which the products of the xylo-oligosaccharide hydrolysis step are located. In indirect cooling embodiments, the products of the xylo-oligosaccharide hydrolysis step are not directly in contact with, and therefore do not mix with, the cooling fluid. The term "cooling fluid" as used herein includes solids, liquids, gases, and combinations thereof. In either direct or indirect cooling embodiments, cooling may be accomplished by means other than use of a cooling fluid, for example by induction. The term "heat exchange" as used herein includes direct cooling, indirect cooling, and combinations thereof.

Additional Embodiments

In one embodiment, the method of treating biomass comprises:

a pretreatment step, wherein said biomass is contacted with a first supercritical, near-critical, or sub-critical fluid to form a pretreated slurry comprising a solid matrix and a first liquid fraction comprising xylo-oligosaccharides;
wherein said first supercritical, near-critical, or sub-critical fluid comprises water and, optionally, $CO_2$; and
wherein said first supercritical, near-critical, or sub-critical fluid is substantially free of $C_1$-$C_5$ alcohol;
a first separation step, wherein said solid matrix and said first liquid fraction are separated;
a first hydrolysis step, wherein said solid matrix is contacted with a second supercritical or near-critical fluid to form a insoluble lignin-containing fraction and a second liquid fraction comprising cello-oligosaccharides;
wherein said second supercritical or near-critical fluid comprises water and, optionally, $CO_2$; and
wherein said second supercritical or near-critical fluid is substantially free of $C_1$-$C_5$ alcohol;
a second separation step, wherein said insoluble lignin-containing fraction and said second liquid fraction are separated; and
a second hydrolysis step, wherein said second liquid fraction is contacted with a third near-critical or sub-critical fluid to form a product comprising glucose monomers;
wherein said third near-critical or sub-critical fluid comprises water and, optionally, acid, preferably an inorganic acid.

In another embodiment, the method of treating biomass comprises:

a pretreatment step, wherein said biomass is contacted with a first supercritical, near-critical, or sub-critical fluid to form a pretreated slurry comprising a solid matrix and a first liquid fraction comprising xylo-oligosaccharides;
wherein said first supercritical, near-critical, or sub-critical fluid comprises water and, optionally, $CO_2$; and
wherein said first supercritical, near-critical, or sub-critical fluid is substantially free of $C_1$-$C_5$ alcohol;
a first separation step, wherein said solid matrix and said first liquid fraction are separated;
a first hydrolysis step, wherein said solid matrix is contacted with a second supercritical or near-critical fluid to form a insoluble lignin-containing fraction and a second liquid fraction comprising cello-oligosaccharides;
wherein said second supercritical or near-critical fluid comprises water and, optionally, $CO_2$; and
wherein said second supercritical or near-critical fluid is substantially free of $C_1$-$C_5$ alcohol;
a second separation step, wherein said insoluble lignin-containing fraction and said second liquid fraction are separated; and
a second hydrolysis step, wherein said second liquid fraction is contacted with a third near-critical or sub-critical fluid to form a product comprising glucose monomers;
wherein said third near-critical or sub-critical fluid comprises water and, optionally, $CO_2$.
a third hydrolysis step, wherein said first liquid fraction is contacted with a fourth near-critical or sub-critical fluid to form a second product comprising xylose monomers;
wherein said fourth near-critical or sub-critical fluid comprises water and, optionally, acid, preferably inorganic acid.

In yet other embodiments, the invention is directed to methods of increasing the level of xylose produced from biomass, comprising:

fractionating said biomass to form:
a solid fraction comprising:
cellulose; and
insoluble lignin; and
a first liquid fraction at a first temperature and at a first pressure comprising:
a soluble $C_5$ saccharide selected from the group consisting of xylo-oligosaccharides, xylose, and mixtures thereof;
separating said solid fraction from said first liquid fraction at a second pressure;
wherein said first pressure and said second pressure are substantially the same (preferably, said second temperature is less than said first temperature);
adding to said first liquid fraction an aqueous acid to increase the level of said soluble $C_5$ saccharide in said liquid fraction to form a second liquid fraction at a second temperature; and
optionally, hydrolyzing said second liquid fraction to form xylose.

In certain embodiments, said xylo-oligosaccharides in said first liquid fraction have about 2 mer units to about 25 mer units; and said xylo-oligosaccharades in said second liquid fraction have about 2 mer units to about 15 mer units. In certain preferred embodiments, the yield of said xylose is at least 70% of theoretical yield. In certain embodiments, said aqueous acid is selected from the group consisting of an organic acid and an inorganic acid. Suitable inorganic acids include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. The acid may be selected from the group consisting of hydrofluoric acid, hydrochloric acid, hydrobromic acid, hydroiodic acid, sulfuric acid, sulfonic acid, phosphoric acid, phosphonic acid, nitric acid, nitrous acid, and combinations thereof. Preferably, said inorganic acid is dilute sulfuric acid. The amount of acid may be present in an amount from about 0.1% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In yet other embodiments, the invention is directed to methods of increasing the level of glucose produced from lignocellulosic biomass, comprising:
providing a fractionated biomass (preferably, under pressure greater than ambient), comprising:
a first solid fraction comprising:
cellulose; and
insoluble lignin; and
a first liquid fraction;
mixing said solid fraction with water to form a slurry;
pre-heating said slurry to a temperature less than critical point of water;
contacting said slurry with a second reaction fluid to form:
a second solid fraction comprising:
insoluble lignin; and
a second liquid fraction comprising:
a saccharide selected from the group consisting of cello-oligosaccharides, glucose, and mixtures thereof;
wherein said second reaction fluid comprises water and, optionally, carbon dioxide, said second reaction fluid having a temperature and a pressure above the critical point of water and of carbon dioxide; and
reducing the temperature of said reaction mixture to a temperature below the critical point of water; and
optionally, hydrolyzing said second liquid fraction to form glucose.
Preferably, the method is continuous. In certain embodiments, reducing the temperature of said reaction mixture to a temperature below the critical point of water comprises contacting said reaction mixture with a composition comprising water. In other embodiments, the temperature of said reaction mixture to a temperature below the critical point of water comprises contacting said reaction mixture with a composition comprising water and acid at a level less than about 10%, preferably less than about 5%, more preferably less than about 2%, and even more preferably, less than about 1%, by weight, based on the total weight of said composition. In certain embodiments, said fractionated biomass is prepared by contacting said biomass with a first reaction fluid, comprising water and, optionally, carbon dioxide, said first reaction fluid having a temperature and a pressure above the critical point of carbon dioxide, and at least one of said temperature and said pressure of said first reactive fluid being below the critical temperature and the critical temperature of water. In certain embodiments, said pre-heating is carried out at a temperature of about 245° C. to about 255° C. and a pressure of about 200 bar to about 260 bar. In certain embodiments, said contacting said slurry with a second reaction fluid is carried out at a temperature of about 358° C. to about 380° C. and a pressure of about 200 bar to about 260 bar. In certain embodiments, said reducing the temperature of said reaction mixture is carried out at a temperature of about 260° C. to about 280° C. and a pressure of about 200 bar to about 260 bar. In certain preferred embodiments, the yield of said glucose is at least about 63% of theoretical yield. In certain aspects, the method yields a composition, comprising:
glucose of at least about 63%, by weight, based on the total weight of the composition;
water;
less than about 13.0% glycolaldehyde, by weight, based on the total weight of the composition;
less than about 2.0% glycolic acid, by weight, based on the total weight of the composition; and
wherein said glucose is extracted from biomass using supercritical fluid extraction.

In one embodiment, an extruder is used for one or more of: a conveyer, a reactor, and a heat exchanger for one or more of the biomass pretreatment and a hydrolysis steps. In one embodiment, an extruder is used as a conveyer, a reactor, and a heat exchanger. In one embodiment, a first extruder is used as a conveyer, reactor, and/or a heat exchanger for biomass pretreatment, and a second extruder is used as a conveyer, reactor, and/or a heat exchanger for a hydrolysis step. In a related embodiment, a third extruder is used as a conveyer, reactor, and/or a heat exchanger for a second hydrolysis step.

In one embodiment, an extruder comprises one or more screws. In another embodiment, an extruder comprises two screws. In another embodiment, an extruder comprises more than two screws. In another embodiment, two or more screws of an extruder co-rotate. In a related embodiment, the two or more screws counter-rotate.

Apparatus

FIG. 1 shows a schematic of one embodiment of the apparatus of the invention for converting lignocellulosic biomass 102 to xylose (solution form) 107, glucose (solution form 115), and lignin (solid form) 116. Lignocellulosic biomass 102 is pretreated in a pretreatment reactor 101 using hot compressed water (HCW) 103 (where the hot compressed water is under sub-critical conditions) and, optionally supercritical $CO_2$ 104 to hydrolyze hemicellulose to hemicellulosic sugars, e.g., xylose and xylo-oligosaccharides. The resultant slurry 105 is subjected to solid/liquid (S/L) separation 106; the liquid phase contains hemicellulosic sugars and the solid phase contains mostly glucan and insoluble lignin. Optionally, acid 108, preferably, inorganic acid (such as sulfuric acid), may be added separately or as part of quenching fluid, not shown. The yields of hemicellulosic sugars in the liquor and of glucan and lignin in the solid phase are typically ≥80%, ≥90%, and ≥90% (of theoretical), respectively. This solid matrix 109 is mixed with water, and optionally preheated, then subjected to hydrolysis in a hydrolysis reactor 110 using supercritical and near-critical fluids. Supercritical water (SCW) 111 and supercritical $CO_2$ 112 (and optionally acid 113) act upon glucan to selectively hydrolyze it while majority of the lignin stays insoluble. After solid/liquid separation 114, liquid phase containing hexose sugars 115 and solid phase containing mostly lignin 116 are obtained. Optionally, an acid 113, preferably an inorganic acid (such as sulfuric acid), can be added as well that enhances cellulose hydrolysis while retarding lignin solubilization. The lignin serves as fuel 117 (such as used in a boiler, not shown) whereas hexose and pentose sugars are feedstocks fermentations and in deriving high-value intermediates and chemicals.

In one embodiment, an apparatus for converting biomass comprises (a) a pretreatment reactor and (b) a hydrolysis reactor. In a related embodiment, the hydrolysis reactor is associated with the pretreatment reactor. In a related embodiment, the hydrolysis reactor is associated with the pretreatment reactor and is adapted such that pretreated biomass is conveyed from the pretreatment reactor to the hydrolysis reactor. In a related embodiment, biomass is conveyed from the pretreatment reactor to the hydrolysis reactor using an extruder, an eductor, or a pump. In one embodiment an extruder delivers pretreated biomass from the pretreatment reactor to the hydrolysis reactor. In a related embodiment, the extruder comprises a screw rotatably associated with a motor. In another related embodiment, the extruder comprises two screws (a "twin-screw extruder"). In one embodiment, the extruder has variable-pitch screws.

In one embodiment, a first reactor is adapted to feed one or more products of a first reaction to a second reactor. For example and without limitation, a pretreatment reactor is adapted to feed a solid matrix into a hydrolysis reactor. In one embodiment, the first reactor is adapted such that one or more reacted products is continuously fed into a second reactor. In a related embodiment, an extruder is associated with the first reactor, said extruder adapted to feed one or more reacted products into a second reactor. In a related embodiment, the extruder is a twin-screw extruder. In another embodiment, the first reactor comprises an extruder. In a related embodiment, at least a portion of the extruder is adapted to separate two or more reacted products. For example and without limitation, a pretreatment reactor comprising an extruder is adapted such that at least a portion of the extruder separates pretreated biomass into a first liquid fraction and a solid matrix; and said extruder is further adapted to feed said solid matrix into a hydrolysis reactor. In another embodiment, an eductor is associated with the pretreatment reactor and is adapted to feed one or more reaction products from a first reactor into a second reactor. In a related embodiment, steam is used to force said one or more reaction products from the first reactor into the second reactor. In a related embodiment, the eductor comprises a steam inlet through which a relatively high pressure of steam is introduced, and wherein the one or more reaction products from the first reactor is transferred to the second reactor in response to an elevated pressure of steam in the eductor.

In one embodiment, a reactor comprises an extruder in which at least a portion of a reaction occurs. In a related embodiment, the extruder is a twin-screw extruder, optionally with variable-pitch screws.

Figure 3:
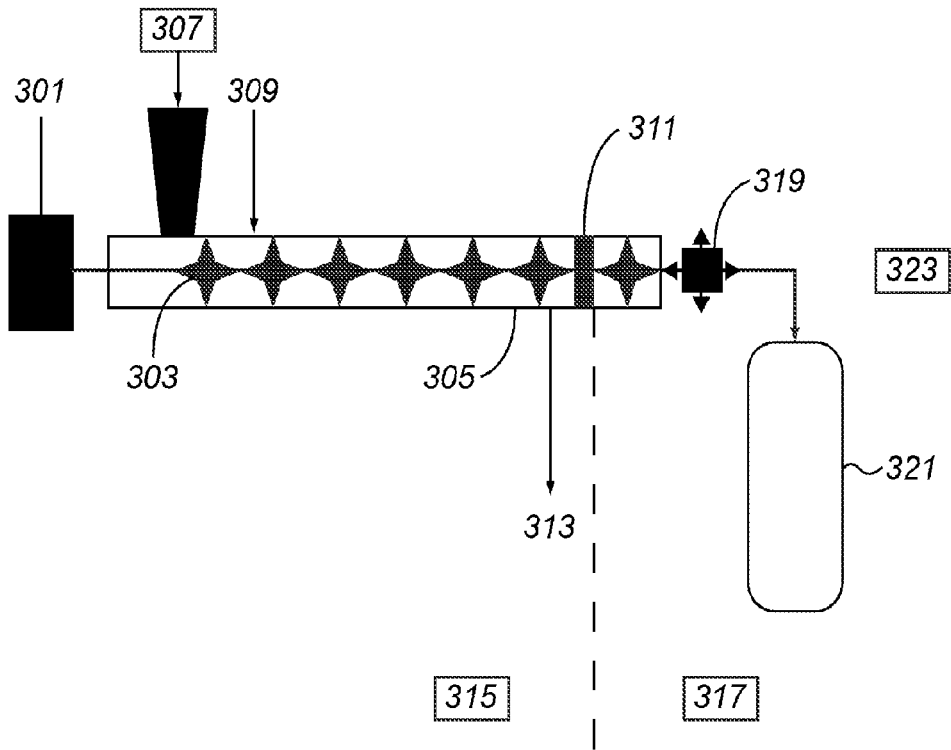
FIG. 3 depicts a schematic representation of introduction of biomass into a pretreatment reactor by extrusion according to one embodiment of the present invention.
Figure 4:
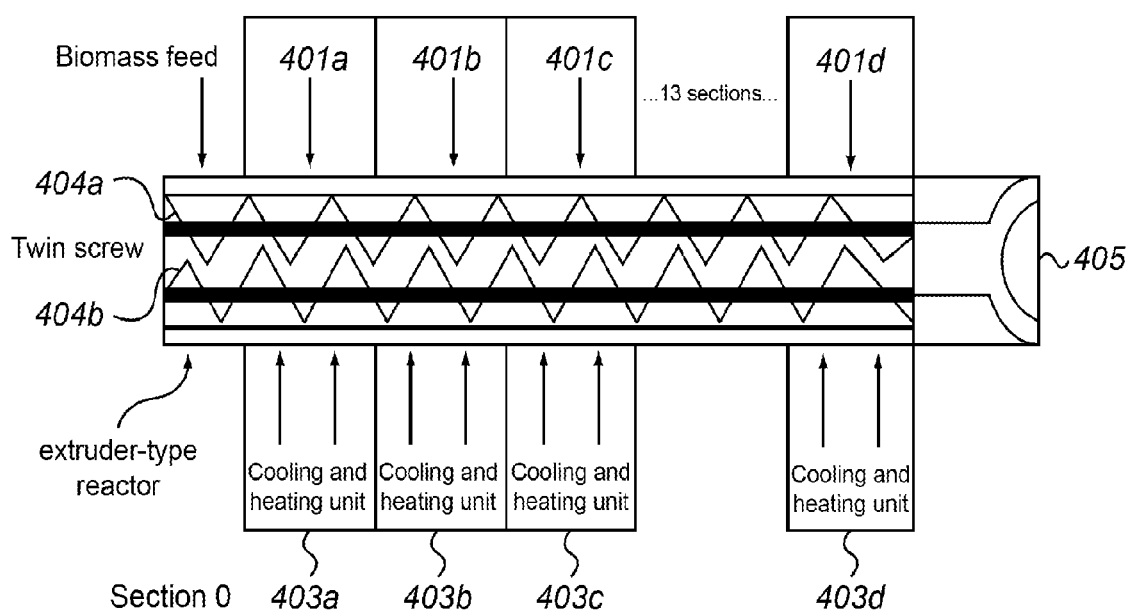
FIG. 4 is a cutaway representation of a twin-screw extruder useful to introduce biomass into a pretreatment reactor in one embodiment of the present invention.

In one embodiment, a reactor is adapted to separate the products of the reaction that occurs in the reactor. For example and without limitation, a hydrolysis reactor is adapted to separate a second liquid fraction and a insoluble lignin-containing fraction after hydrolysis of solid matrix occurs in the hydrolysis reactor. In a related embodiment, a reactor comprises an extruder in which at least a portion of a reaction occurs and in which at least a portion of the reacted products are separated into their component parts. This is shown generally in FIG. 3, where a motor 301 is used to drive an extruder screw 303 within an extruder barrel 305 to move biomass (not shown) that is fed through the biomass feed 307. A dynamic plug 311 of extruded biomass is formed, creating a low pressure zone 315 prior to the plug and a high pressure zone 317 beyond the plug in the extruder barrel. Wetting fluid 309, in this case water, is added to the extruder barrel. The liquid fraction is squeezed from the wet extruded biomass (squeezate liquor 313) prior to the dynamic plug. The solid fraction 323 (for example, at 45-50% solids) exits through the discharge valve 319 into a reactor 321 for further treatment. In a related embodiment, extrusion occurs in an extruder. In a related embodiment, an extruder used to separate the solid fraction and liquid fraction comprises one to a plurality of screws. In a related embodiment, the extruder includes two screws (a "twin-screw extruder"), as shown in FIG. 4 with an extruder-type reactor 402 with twin screws 404a and 404b that move the biomass that is introduced via the biomass feed 406 through the extruder, process it before it exits the extruder, and is controlled by a pressure control valve 405. In another embodiment, the reactor comprises a drain through which a liquid fraction exits the reactor.

In one embodiment, a reactor comprises a water inlet which is adapted to allow water to be introduced or injected into the reactor. The reactor may be used for pretreatment of biomass, hydrolysis of a solid matrix, hydrolysis of a liquid fraction, etc. In a related embodiment, water is introduced into the reactor through the water inlet to quench a pretreatment or hydrolysis reaction. In a related embodiment, water is introduced through a water inlet after at least a portion of the contents have been reacted (e.g., pretreated or hydrolyzed). In an embodiment where the reactor comprises an extruder, said reactor has a reaction zone defined as the portion of the length of the extruder in which the pretreatment or hydrolysis reaction occurs. In such an embodiment biomass, solid matrix, or a liquid fraction enters the reaction zone at a first end and pretreatment or hydrolysis occurs as the material is forced through the reaction zone towards a second end. In another embodiment, a water inlet is positioned on an extruder-type reactor at least halfway between said first end and said second end, at least $5/8$ of the way between said first end and said second end, at least $2/3$ of the way between said first end and said second end, at least $3/4$ of the way between said first end and said second end, or at least $7/8$ of the way between said first end and said second end.

In one embodiment, a reactor comprises a plurality of units 401a, 401b, 401c, and 401d, adapted to allow water to be introduced or injected into the reactor, for example, as shown in FIG. 4. The reactor may be used for pretreatment of biomass, hydrolysis of a solid matrix, hydrolysis of a liquid fraction, etc. In a related embodiment, water is introduced into the reactor through at least one of the plurality of water injection units to adjust at least one of the temperature and pressure of the reactor. In a related embodiment, said water injection units are associated along the length of an extruder-type reactor 402, as shown in FIG. 4. In another related embodiment, a fluid comprising water and at least one other component is introduced into the reactor through at least one of the plurality of water injection units. In another embodiment, the fluid comprising water has at least one of a known temperature and a known pressure.

In one embodiment, a reactor comprises one or more temperature control units 403a, 403b, 403c, and 403d adapted to monitor the temperature of a reaction which occurs in the reactor, for example, as shown in FIG. 4. The reactor may be used for pretreatment of biomass, hydrolysis of a solid matrix, hydrolysis of a liquid fraction, etc. In a related embodiment, said temperature control units are associated with one or more water injection units. In a related embodiment, the temperature control units are adapted such that when the temperature of the reaction falls outside a predetermined temperature range, said temperature control units cause one or more water injection units to allow introduction of a fluid. In a related embodiment, the temperature and/or pressure of the fluid to be injected into the reactor is known. In another related embodiment, any one of a plurality of temperature control units is associated with a single water injection unit. In another related embodiment, any one of a plurality of water injection units is associated with a single temperature control unit. In another embodiment, any one of a plurality of temperature control units is associated with one of a plurality of water injection units and vice versa.

In one embodiment, a pretreatment reactor comprises a conical reactor 901, such as shown in FIG. 9. In addition to use as a pretreatment reactor, the reactor may be alternatively be used for hydrolysis of a solid matrix, hydrolysis of a liquid fraction, etc. In a related embodiment, the conical reactor comprises a conical-shaped reaction vessel defined by an axis, a radius, and an inner periphery; and a mixing mechanism (for example, impeller 902 and motor 903. In a related embodiment, the mixing mechanism comprises an arm which rotates about the axis of the conical reactor and substantially parallel with the radius of the conical reactor, a first motor operatively associated with said arm, an impeller defined by an impeller axis and associated with said arm and with a second motor, whereby the impeller rotates about its own impeller axis and substantially parallel to the inner periphery of the conical reactor. In a related embodiment, the first and second motors comprise a single motor. In another related embodiment, the impeller further comprises an impeller shaft extending substantially along the impeller axis and at least one impeller blade circumferentially associated with said impeller shaft. In a related embodiment, the impeller comprises one impeller blade. In a related embodiment, said impeller blade is helically associated with the impeller shaft.

In one embodiment, the apparatus for converting biomass comprises:

a pretreatment reactor adapted to pretreat biomass;

a first hydrolysis reactor associated with said pretreatment reactor and adapted to hydrolyze a solid matrix formed in the pretreatment reactor;

a second hydrolysis reactor associated with said pretreatment reactor and adapted to hydrolyze a first liquid fraction formed in the pretreatment reactor; and optionally, a third hydrolysis reactor associated with said first hydrolysis reactor and adapted to hydrolyze a second liquid fraction formed in said first hydrolysis reactor.

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Continuous Pretreatment of Biomass

Figure 2:
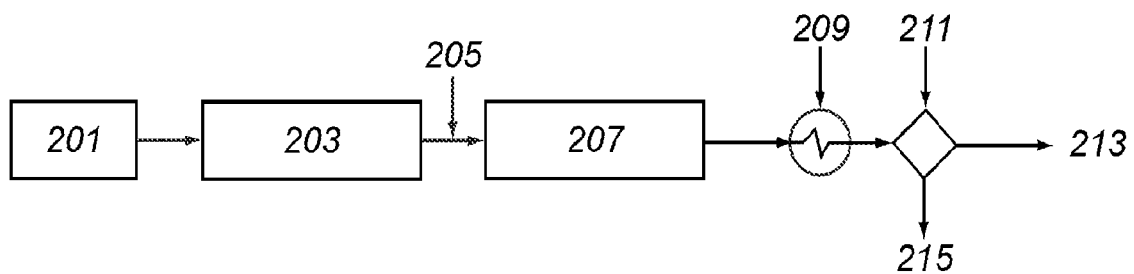
FIG. 2 is a block diagram showing one embodiment of the biomass pretreatment portion of the present invention.
Figure 14:
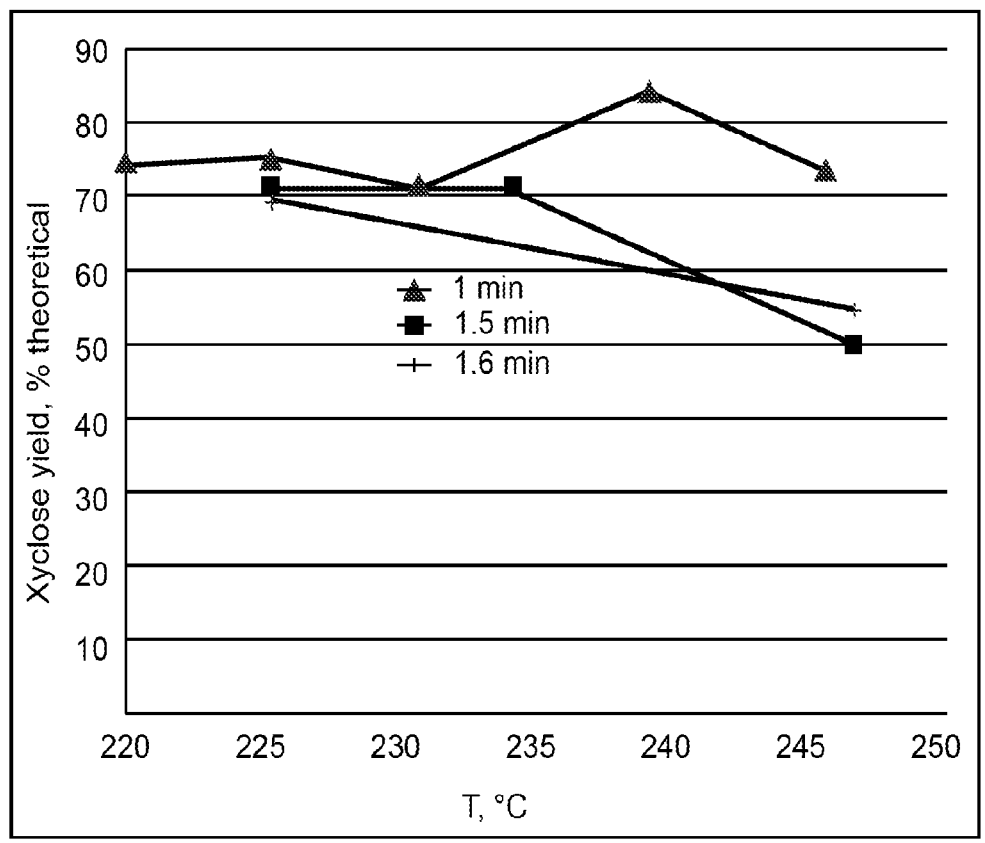
FIG. 14 shows total xylose monomer yields (as a percentage of the theoretical maximum xylose yield) as a function of hydrolysis temperature at various residence times according to one embodiment of the present invention (continuous pretreatment of biomass).

A continuous pilot-scale system with a 100 kg/d (dry basis) capacity was used. A schematic of the pretreatment setup is shown in FIG. 2. Biomass slurry in water 201 is fed into a furnace 203 and heated. Optionally, carbon dioxide 205 is introduced as a supercritical fluid with supercritical $CO_2$ being a catalyst into the pretreatment reactor 207. After pretreatment, the fractionated biomass is cooled by the introduction of cooling fluid 209, such as water (with or without acid, preferably an inorganic acid). The liquid fraction 215 containing the xylose is separated using a solid/liquid separator 211 from the solid fraction 213 containing cellulose and lignin Experiments were conducted in the temperature range of 220-250° C., pressure of 100 bar and residence times of 1-1.6 minutes. FIG. 14 shows yields on incoming feed basis; the feed containing ~35% glucan, ~18% xylan and ~30% lignin (mixed hardwoods).

Example 2

Continuous Cellulose Hydrolysis Using Supercritical and Near-Critical Water

Figure 7:
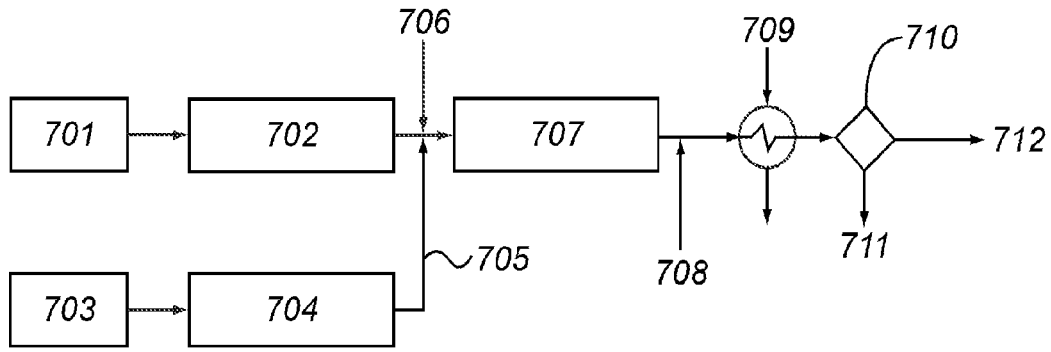
FIG. 7 depicts a schematic representation of treatment of a solid matrix produced from pretreatment of biomass according to one embodiment of the present invention.

A continuous pilot-scale system with a 100 kg/d (dry basis) capacity was used. Schematic of the cellulose hydrolysis setup is shown in FIG. 7. The pretreated biomass slurry 701 is first preheated in a furnace 702 then directly subjected to hydrolysis in a hydrolysis reactor 707 using supercritical and near-critical fluids. Supercritical water (SCW) 705 (prepared by heating a water stream 703 in a furnace 704 under pressure) and supercritical $CO_2$ 706 (and optionally acid, not shown) act upon glucan to selectively hydrolyze it while majority of the lignin stays insoluble. The hydrolyzed slurry is quenched with, for example, water quench 708 (with or without dilute acid, preferably an inorganic acid, such as sulfuric acid) to slow the down the hydrolysis reaction and prevent the formation of degradation products. The use of acid in the quench also hydrolyzes the cello-oligosaccharides to glucose monomers. The hydrolyzed slurry is further cooled with cooling fluid, such as water 709. After solid/liquid separation 710, liquid phase containing hexose sugars 711 and solid phase containing mostly lignin 712 are obtained. Experiments were conducted in the temperature range of 360-374° C., pressure of 225 bar and residence time of 1 s. $CO_2$ was introduced into the slurry (4 wt %), supercritical $CO_2$ being a catalyst. The temperature is maintained for a desired residence time by directly quenching the reaction by injection of cold water. Table 1 and Table 2 show yields on incoming feed basis; the feed containing ~55% glucan and ~40% lignin (pretreated solids), for residence times of 1 s and 1.2 s, respectively. All yields are % of theoretical and refer to those in the liquor except for lignin which is in the solid phase. Cellulose hydrolysis and lignin solubilization are inversely correlated. Glycolaldehyde and glycolic acid are also produced in meaningful quantities and can be separated as valuable products.

TABLE 1

Results from continuous cellulose hydrolysis

| Temperature (° C.) | Pressure (bar) | Glucose oligomer (%) | Total C6 sugar (%) | Glycolaldehyde (%) | Glycolic acid (%) | Other Acids (%) | Lignin Recovery (%) |
|---|---|---|---|---|---|---|---|
| 353 ± 2.5 | 222 ± 5.7 | 59.5 | 60.6 | 7.4 | NA | 8.0 | 50-70 |
| 364 ± 2.5 | 224 ± 7.4 | 59.1 | 60.1 | 8.6 | 1.9 | 7.9 | 50-70 |

TABLE 1-continued

Results from continuous cellulose hydrolysis

| Temperature (° C.) | Pressure (bar) | Glucose oligomer (%) | Total C6 sugar (%) | Glycolaldehyde (%) | Glycolic acid (%) | Other Acids (%) | Lignin Recovery (%) |
|---|---|---|---|---|---|---|---|
| 367 ± 2.0 | 226 ± 7.0 | 63.0 | 63.8 | 10.9 | 3.7 | 12.4 | 50-70 |
| 370 ± 2.2 | 231 ± 7.1 | 59 | 60.5 | 12.8 | 1.6 | 13.4 | 50-70 |

Preheat Stage: 250° C./20 s
Cellulose Hydrolysis Stage: 2 s

Example 3

Figure 15:
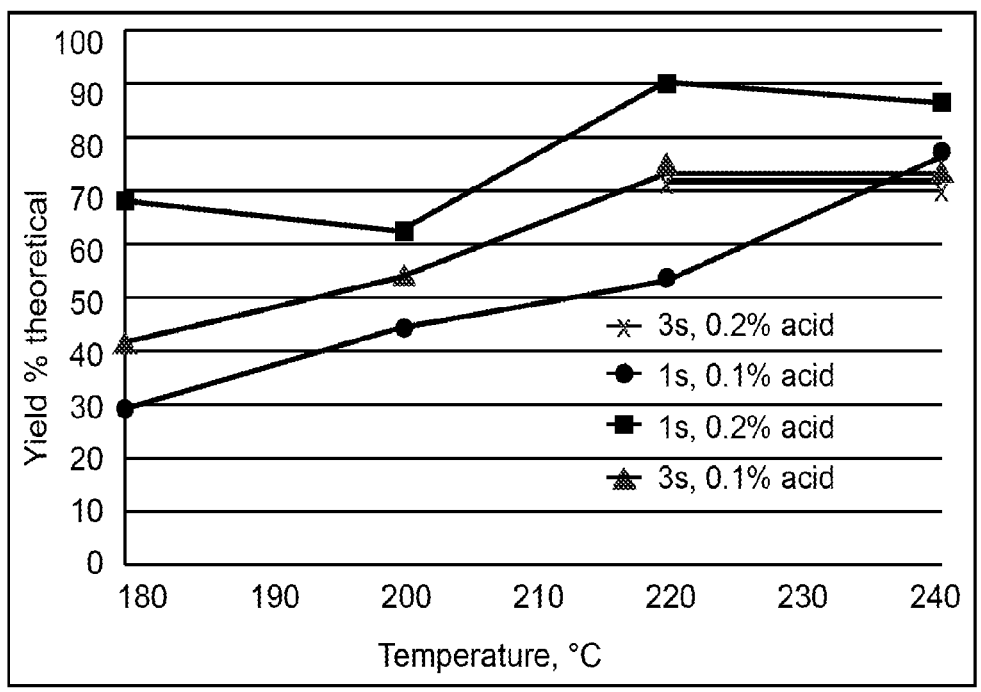
FIG. 15 shows xylose monomer yields (as a percentage of the theoretical maximum xylose yield) as a function of hydrolysis temperature at various residence times with varying levels of sulfuric acid according to one embodiment of the present invention.

Continuous Conversion of Xylo-Oligosaccharides (XOS)-to-Xylose Monomers Using Acid and Hot Compressed Water A continuous system with a 10 kg/d (dry basis) capacity was used. Schematic of the setup was similar to that shown in FIG. 2. Xylose liquor produced from a pretreatment operation similar to Example 1 was used as starting material. Experiments were conducted in the temperature range of 180-240° C., pressure of 100 bar and residence time of 1-3 s. $H_2SO_4$ at 0.1%-0.2% (pH=1.7-2.0) was introduced into the liquor as a catalyst. Results show that ~90% monomeric xylose yield can be achieved in 1 s using 0.2% acid (FIG. 15).

Example 4

Figure 13:
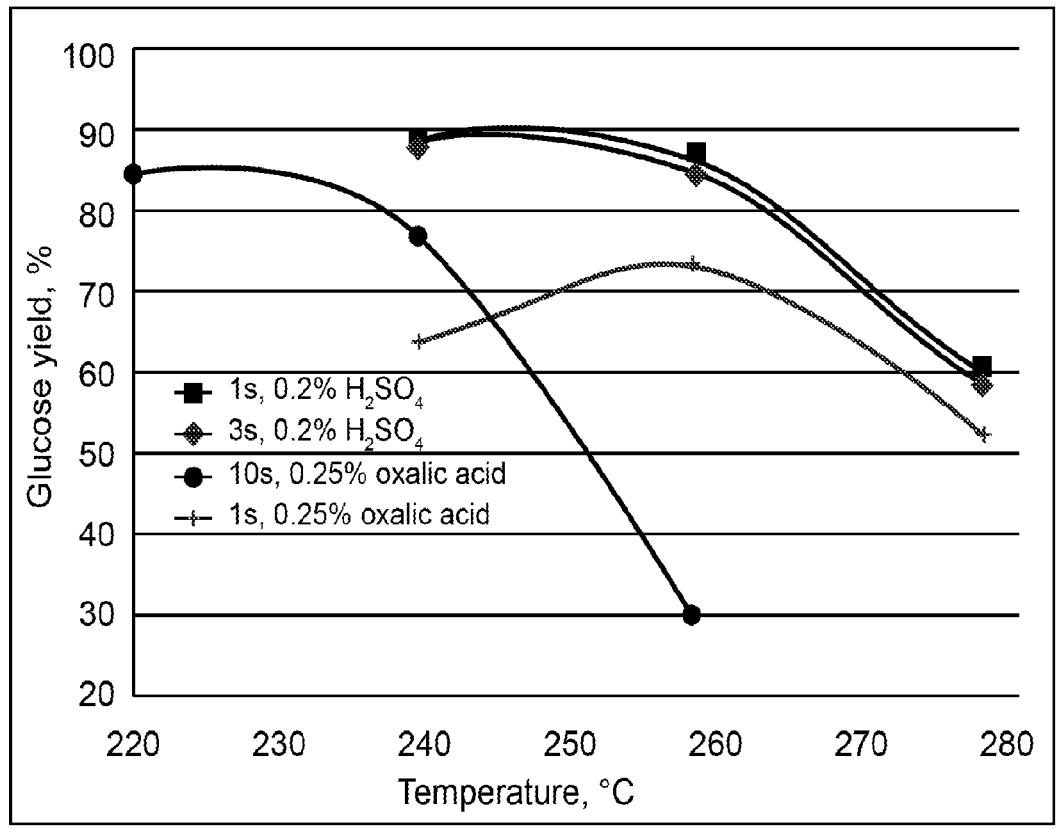
FIG. 13 shows typical glucose monomer yields (as a percentage of the theoretical maximum glucose yield) as a function of hydrolysis temperature according to one embodiment of the present invention.

Continuous Conversion of Cello-Oligosaccharides (COS)-to-Glucose Monomers Using Acid and Hot Compressed Water A continuous system with a 10 kg/d (dry basis) capacity was used. A schematic of the setup was similar to that shown in FIG. 2. Slurry produced from a cellulose hydrolysis operation similar to Example 2 was filtered and the resulting liquor was used as starting material. Experiments were conducted in the temperature range of 200-260° C., pressure of 100 bar and residence time of 1-3 s. $H_2SO_4$ at 0.2% or oxalic acid at 0.25% was introduced into the liquor as a catalyst. Results show that ~90% monomeric glucose yield can be achieved in 1 s using 0.1% sulfuric acid, as shown in FIG. 13.

Example 5

Figure 12:
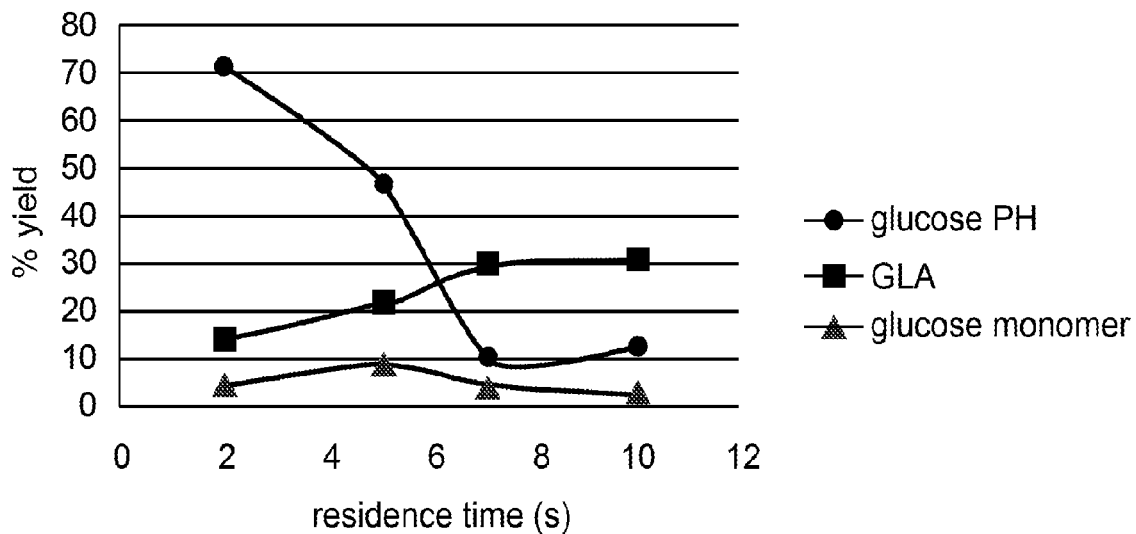
FIG. 12 shows yields (as a percentage of theoretical maxima for each component) for certain components of a mixture produced by treatment of a pretreated solid matrix at 377° C. as a function of residence time according to one embodiment of the present invention.

Effect of Cellulose Hydrolysis Residence Time on Production of Glucose and Byproducts Continuous cellulose hydrolysis was carried out at 377° C. on the solid matrix prepared by the pretreatment step described above at different residence times (1.6 s, 5 s, 7 s, and 10 s). Yields (as a percentage of theoretical maxima for each component) were measured for certain components (glucose, glucose post hydrolysis (PH), glycolaldehyde (GLA), and sum of glucose (PH) and GLA. The results are shown in FIG. 12, where glucose is shown as a diamond, glucose PH is shown as a triangle, glycolaldehyde (GLA) is shown as a square, and sum of glucose (PH) and GLA is shown as an X. As residence time increases, the level of total glucose (glucose PH) decreases and the level of glycolaldehyde increases. Thus, it is possible to tune the process to yield more sugar (glucose) or to yield more byproducts (such as glycoladehyde).

Glycolaldehyde may be easily hydrogenated to mono-ethylene glycol (MEG), using Raney nickel catalyst, for example. In addition, glycolic acid, glycerolaldehyde, lactic acid, and acetic acid are generated, which may be isolated using, for example, liquid-liquid extraction.

Ethanol fermentation was conducted using glucose liquor produced from the 1.6 s residence time. The liquor, after treatment with activated carbon and overliming treatments, was fermentable to high yields. The results are shown in Table 2.

TABLE 2

Ethanol fermentation using glucose liquor

| Time (hours) | Ethanol (% yield) |
|---|---|
| 24 | 67 |
| 48 | 85 |

Example 6

Effect of $CO_2$ on Production of Glucose and Byproducts

Continuous cellulose hydrolysis with and without $CO_2$ was carried out at 377° C. with a 1.6 s residence time on the solid matrix prepared by the pretreatment step described above. The results are shown in Table 3.

TABLE 3

Effect of $CO_2$

| | Level of $CO_2$ | |
|---|---|---|
| | 5% | 0% |
| Glucose as is (%) | 3.1 | 3.8 |
| Glucose total (%) | 64.8 | 66.8 |
| Glycolaldehyde (%) | 9.2 | 8.8 |
| Glycolic acid and glycolaldehyde (%) | 1.7 | 2.4 |
| Lactic acid (%) | 2.1 | 1.7 |
| Formic acid (%) | 3.2 | 2.8 |
| Acetic acid (%) | 2.2 | 1.7 |
| Lignin recovery (%) | 70.2 | 69.7 |

As can be seen, the difference of the various levels of products and byproducts produced by the continuous cellulose hydrolysis with and without CO2 were statistically insignificant. Thus, it appears that there is no beneficial effect for glucose yield, byproduct yield, or lignin recovery. Accordingly, it would be beneficial to avoid the cost of $CO_2$ pumping, $CO_2$ compression for recycling, and the additional complexity of including $CO_2$ under supercritical conditions.

Example 7

Effect of $CO_2$ in Pretreatment Step

Figure 5:
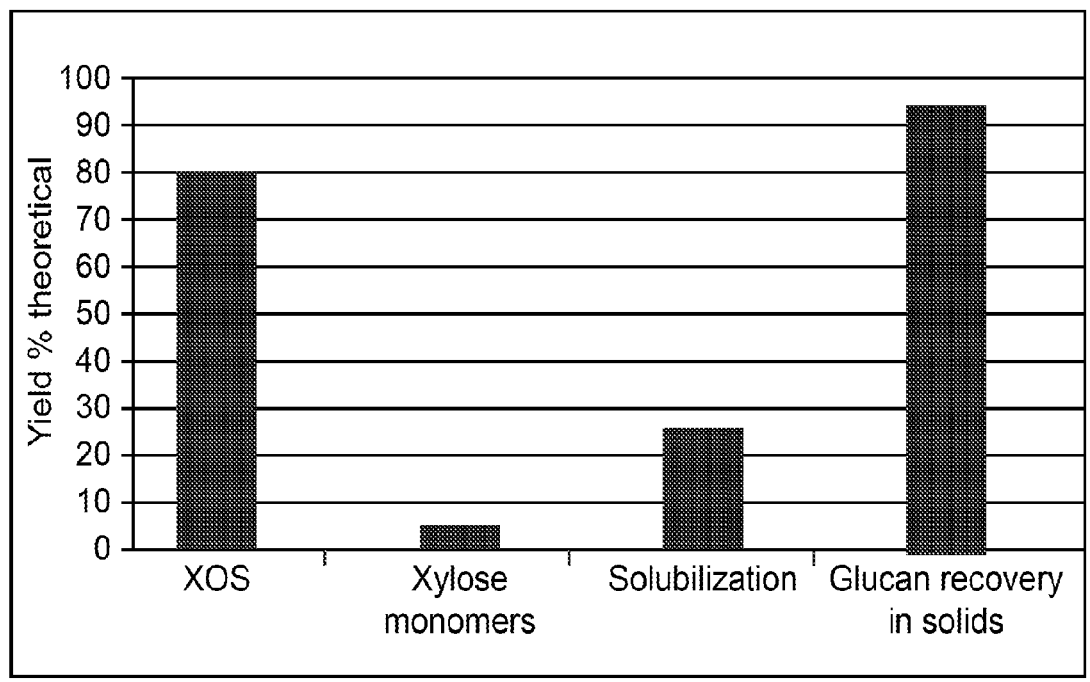
FIG. 5 shows typical yields (as a percentage of theoretical maxima for each component) for certain components of the resulting mixture obtained from pretreatment of biomass according to one embodiment of the present invention.

Pretreatment of biomass with $CO_2$ was carried out at about 230° C. to 240° C. with about 1.5 minutes residence time. The results are shown in FIG. 5 This data shows that there was good xylose recovery in the liquor and glucan recovery in the solids.

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of producing glucose from lignocellulosic biomass, comprising:
   providing a fractionated biomass, comprising:
      a first solid fraction comprising:
         cellulose; and
         insoluble lignin; and
      a first liquid fraction;
   mixing said solid fraction with water to form a slurry;
   optionally, pre-heating said slurry to a temperature less than the critical point of water;
   contacting said slurry with a second reaction fluid to form:
      a second solid fraction comprising:
         insoluble lignin; and
      a second liquid fraction comprising:
         a saccharide selected from the group consisting of cello-oligosaccharides, glucose, and mixtures thereof;
   wherein said second reaction fluid comprises water and, optionally, carbon dioxide, said second reaction fluid having a temperature and a pressure above the critical point of water and of carbon dioxide; and
   reducing the temperature of said reaction mixture to a temperature below the critical point of water; and
   optionally, hydrolyzing said second liquid fraction to form glucose.

2. The method of claim 1, wherein said method is continuous.

3. The method of claim 1, wherein said reducing the temperature of said reaction mixture to a temperature below the critical point of water comprises contacting said reaction mixture with a composition comprising water.

4. The method of claim 1, wherein said reducing the temperature of said reaction mixture to a temperature below the critical point of water comprises contacting said reaction mixture with a composition comprising water and acid at a level less than about 10%, by weight, based on the total weight of said composition.

5. The method of claim 1, wherein said fractionated biomass is prepared by contacting said biomass with a first reaction fluid comprising: water, and
optionally, carbon dioxide;
said first reaction fluid having a temperature and a pressure above the critical point of carbon dioxide, and at least one of said temperature and said pressure of said first reaction fluid being below the critical temperature and the critical pressure of water.

6. The method of claim 1, wherein said pre-heating is performed.

7. The method of claim 6, wherein said pre-heating is carried out at a temperature of about 245° C. to about 255° C. and a pressure of about 200 bar to about 260 bar.

8. The method of claim 1, wherein said contacting said slurry with a second reaction fluid is carried out in a hydrolysis step, and said hydrolysis step occurs at a temperature of about 358° C. to about 380° C. and a pressure of about 200 bar to about 260 bar.

9. The method of claim 1, wherein said reducing the temperature of said reaction mixture is carried out at a temperature of about 260° C. to about 280° C. and a pressure of about 200 bar to about 260 bar.

10. The method of claim 1, wherein the yield of said glucose is at least about 63% of theoretical yield.

11. The method of claim 1,
wherein said hydrolyzing said second liquid fraction is performed;
wherein said hydrolyzing comprises contacting said second liquid fraction with hot compressed water, or a third near-critical or sub-critical fluid, to produce a third liquid fraction comprising glucose monomers;
wherein said third near-critical or sub-critical fluid comprises water; and
optionally, wherein said hot compressed water or said third near-critical or sub-critical fluid comprises acid.

12. The method of claim 11, wherein said acid is present in an amount of about 0.1% to about 1.5% by weight, based on the weight of said hot compressed water, or said third near-critical or sub-critical fluid, whichever is employed in said hydrolyzing said second liquid fraction.

13. The method of claim 11,
wherein said hydrolyzing employs said hot compressed water; and
said hot compressed water has a temperature of about 50° C. to about 250° C. and a pressure sufficient to maintain said hot compressed water in a liquid state.

14. The method of claim 13, wherein said hot compressed water comprises acid.

15. The method of claim 1,
wherein said first liquid fraction comprises xylo-oligosaccharides,
wherein said first liquid fraction is contacted with a second hot compressed water, or a fourth near-critical or sub-critical fluid, to produce a fourth liquid fraction comprising xylose monomers;
wherein said fourth near-critical or sub-critical fluid comprises water; and
optionally, wherein said second hot compressed water or said fourth near-critical or sub-critical fluid comprises acid.

16. The method of claim 15,
wherein said acid is present in an amount of about 0.1% to about 1.5% by weight, based on the weight of said second hot compressed water, or said fourth near-critical or sub-critical fluid, whichever is employed.

17. The method of claim 15,
wherein said first liquid fraction is contacted with said second hot compressed water; and
said second hot compressed water has a temperature of about 50° C. to about 250° C. and a pressure sufficient to maintain said second hot compressed water in a liquid state.

18. The method of claim 17,
wherein said second hot compressed water comprises acid.

19. The method of claim 1,
wherein said reducing the temperature comprises flash cooling.

20. The method of claim 1,
wherein said contacting said slurry is carried out in a hydrolysis step, and said hydrolysis step occurs at a temperature of about 275° C. to about 450° C.

21. The method of claim 20,
wherein said hydrolysis step occurs at a temperature of about 340° C. to about 400° C.

22. The method of claim 20,
wherein said hydrolysis step occurs at a temperature of about 350° C. to about 390° C.

23. The method of claim 20,
wherein said hydrolysis step occurs at a temperature of about 360° C. to about 380° C.

24. The method of claim 20,
wherein said slurry has a residence time in said hydrolysis step of about 1 second to about 10 seconds.

25. The method of claim 20,
wherein said slurry has a residence time in said hydrolysis step of about 1 second to about 45 seconds.

26. The method of claim 20,
wherein said slurry has a residence time in said hydrolysis step of less than about 1 second.

27. The method of claim 1,
wherein said second reaction fluid further comprises carbon dioxide.

28. The method of claim 1,
wherein said second reaction fluid does not include carbon dioxide.

29. The method of claim 1,
wherein said second reaction fluid is substantially free of a C1-C5 alcohol.

30. The method of claim 1,
wherein said hydrolyzing said second liquid fraction is performed,
wherein said hydrolyzing comprises subjecting said second liquid fraction to a temperature of about 220° C. to about 320° C.

* * * * *